(12) United States Patent
Lee et al.

(10) Patent No.: US 11,413,301 B2
(45) Date of Patent: *Aug. 16, 2022

(54) COMPOSITION COMPRISING SEA CUCUMBER EXTRACT AS EFFECTIVE INGREDIENT FOR PREVENTING AND TREATING BRUCH'S MEMBRANE DYSFUNCTION-RELATED DISEASE

(71) Applicant: ALTREGEN CO., LTD., Gyeonggi-do (KR)

(72) Inventors: Yunhee Lee, Jeollabuk-do (KR); Ali Hussain, London (GB); Dae Bong Kim, Seoul (KR)

(73) Assignee: Altregen Co., Ltd., Gyeonggi-do (KR)

( * ) Notice: Subject to any disclaimer, the term of this patent is extended or adjusted under 35 U.S.C. 154(b) by 487 days.

This patent is subject to a terminal disclaimer.

(21) Appl. No.: 16/470,532

(22) PCT Filed: Dec. 18, 2017

(86) PCT No.: PCT/KR2017/014957
§ 371 (c)(1),
(2) Date: Jun. 17, 2019

(87) PCT Pub. No.: WO2018/117572
PCT Pub. Date: Jun. 28, 2018

(65) Prior Publication Data
US 2019/0321381 A1    Oct. 24, 2019

(30) Foreign Application Priority Data

Dec. 19, 2016  (KR) .................. 10-2016-0173715
Dec. 18, 2017  (KR) .................. 10-2017-0174313

(51) Int. Cl.
*A61K 31/704* (2006.01)
*A61K 35/616* (2015.01)

(52) U.S. Cl.
CPC .......... *A61K 31/704* (2013.01); *A61K 35/616* (2013.01)

(58) Field of Classification Search
None
See application file for complete search history.

(56) References Cited

U.S. PATENT DOCUMENTS

| 5,985,330 | A | 11/1999 | Collin | |
| 6,767,890 | B1* | 7/2004 | Collin | C07K 7/06 514/12.2 |
| 7,163,702 | B1 | 1/2007 | Avilov et al. | |
| 2005/0288239 | A1* | 12/2005 | Adrian | A61K 31/704 514/33 |
| 2017/0224159 | A1 | 8/2017 | Ohler et al. | |

FOREIGN PATENT DOCUMENTS

| CN | 1318388 A | 10/2001 |
| CN | 106109499 A | 11/2016 |
| EP | 3556373 A1 | 10/2019 |
| KR | 10-1999-0057561 A | 7/1999 |
| KR | 10-2014-0045261 A | 4/2014 |
| WO | 2005072528 A1 | 8/2005 |
| WO | 2018117572 A1 | 6/2018 |

OTHER PUBLICATIONS

International Search Report and Written Opinion of PCT/KR2017/014957, dated Apr. 24, 2018, 9 Pages.
Booij et al., The Dynamic Nature of Bruch's Membrane, 2010, Progress in Retinal and Eye Research, vol. 29(1), pp. 1-18.

* cited by examiner

*Primary Examiner* — Dale R Miller
(74) *Attorney, Agent, or Firm* — Nixon Peabody LLP; Linda B. Huber

(57) ABSTRACT

The present invention relates to a composition for preventing and treating a Bruch's membrane dysfunction-associated disease, which includes a sea cucumber extract as an active ingredient, and more particularly, to a composition for preventing and treating a Bruch's membrane dysfunction-associated disease, which includes a sea cucumber extract having effects of regenerating the Bruch's membrane of an eye and improving a transport function. The composition according to the present invention improves the transport function of the Bruch's membrane and promotes the regeneration of the Bruch's membrane, thereby delaying or reversing an eye aging process, and thus has excellent effects on the prevention and treatment of a disease such as age-related macular degeneration (AMD), Sorsby's fundus dystrophy, Malattia Levintanese (ML), Stargardt disease, Best's vitelliform retinal dystrophy and Doyne's honeycomb retinal dystrophy (DHRD), which occurs due to the age-related dysfunction of the Bruch's membrane.

15 Claims, 20 Drawing Sheets

A

B

Bruch's membrane. C: Control; SC: 2.5% sea cucumber

COMPOSITION COMPRISING SEA CUCUMBER EXTRACT AS EFFECTIVE INGREDIENT FOR PREVENTING AND TREATING BRUCH'S MEMBRANE DYSFUNCTION-RELATED DISEASE

CROSS-REFERENCE TO RELATED APPLICATIONS

This application is a National Phase of International Application No. PCT/KR2017/014957 filed Dec. 18, 2017, currently pending, which designated the U.S. and that International Application was published under PCT Article 21(2) in English. This application also includes a claim of priority under 35 U.S.C. § 119(a) and § 365(b) to Korean patent application No. KR 10-2016-0173715 filed Dec. 19, 2016, and Korean patent application No. KR 10-2017-0174313 filed Dec. 18, 2017 the entirety of which is hereby incorporated by reference.

TECHNICAL FIELD

The present invention relates to a composition for preventing and treating a Bruch's membrane dysfunction-associated disease, which contains a sea cucumber extract as an active ingredient, and more particularly, to a composition for preventing and treating a Bruch's membrane dysfunction-associated disease, which contains a sea cucumber extract and has effects of regenerating the Bruch's membrane of an eye and improving a transport function.

BACKGROUND ART

Sea cucumber is a generic term for sea cucumbers that are echinoderms from the class Holothuroidea, and the best health food called ginseng in the sea since a large amount of saponins is contained as an active ingredient like ginseng. Sea cucumber is a medicine for compensating for body fluids from ancient times in the East including China, and has been known as a drug that has excellent effects on diabetes and asthma, and can be used to regain energy when a person loses energy and collapses due to a lot of sweating caused by a rise in temperature during summer. In addition, when a part of the body of sea cucumber is cut, the cutting site returns to its original state within three months, and even when the organs are removed, there is an amazing resilience in that a new organ is generated within a month, and therefore, in oriental and folk medicines, it has been known that sea cucumber enhances the phagocytic ability of human mononuclear cells and macrophages, such that it exhibits a full immune function and is effective in wound treatment.

Sea cucumbers are used for child development-promoting food, tonic food for the elderly, post-recovery food, anemia-preventing food for pregnant women, or food for stimulating bowel movements and have received attention as diet food since they contain less fat and sugar. However, there is no study of the effect of a sea cucumber extract on improvement in eye function.

Photoreceptor cells are light detecting cells present in the retina and transport information to the brain to recognize an object in the visual process. Photoreceptor cells are the most metabolically active cells in the body and therefore require efficient delivery of nutrients and removal of waste products. Since these cells operate in an environment rich in essential fatty acids, light, and a high concentration of oxygen, the cells undergo considerable free radical-induced damage. In this case, retinal pigment epithelium (RPE) cells are used to continuously regenerate the outer segments of the damaged photoreceptor cells.

Photoreceptor cells and RPE cells receive nutrients through choroidal blood circulation. When nutrients provided from blood are secreted from choroidal capillaries, before reaching the RPE cells and photoreceptor cells, first, they should pass through an extracellular matrix called the Bruch's membrane. Small-sized nutrients such as glucose, oxygen, amino acids, etc. pass through the Bruch's membrane by simple passive diffusion, and vitamins, trace metals and lipids are bound to carrier proteins, and then separated from the RPE cells through the Bruch's membrane. In contrast, waste generated from photoreceptor cells and the RPE cells is removed from the choroid through the Bruch's membrane. Since the waste is generally toxic, it can damage the Bruch's membrane, and initiate inflammation. Therefore, an efficient material transport ability of the Bruch's membrane is essential for the maintenance of normal vision and survival of photoreceptor cells (FIG. 1).

Due to aging, the thickness of the Bruch's membrane is increased two- to three-fold, and thus the diffusion gradients for exchange of nutrients and waste are reduced, making it difficult to diffuse materials into the Bruch's membrane. Accordingly, lipids, proteo-lipid complexes and waste discarded from RPE cells are deposited on the membrane, the cross-linking of collagen increases, and the amount of denatured collagen increases. In addition, not only amounts of glycosylation-induced glycation products of proteins and lipids (AGE; advanced protein glycation end-products, ALE; advanced lipid glycation end-products) are increased (Handa et al. 1999), but also the deposition of damaged or polymerized protein complexes is also increased, eventually interfering with the transport ability of a membrane (Holz et al. 1994), and adversely affecting the delivery of nutrients and the removal of waste (FIG. 2).

In the case of age-related macular degeneration (AMD), for which aging is a major risk factor, age-related changes become much more serious, the reduced transport ability of the Bruch's membrane leads to the death of RPE cells and photoreceptor cells and thus blindness (FIG. 3).

Clinically, in the aging of the Bruch's membrane in the elderly, diminished scotopic thresholds caused by inefficient regeneration of vitamin A have been reported (Steinmetz et al. 1993; Owsley et al. 2001). Currently, in some countries, administration of vitamin A is prescribed with metals and anti-oxidants, but there are two problems in this strategy. First, only specific nutrients are added, and thus other essential nutrients are still deficient, and secondly, when a metal is added to the Bruch's membrane decreased in transport function, a concentration of the metal in the Bruch's membrane is increased and subsequently deposited in the membrane, resulting in further increasing the damage thereby. In addition, according to the Age-Related Eye Disease Study (AREDS), which is a US macular degeneration clinical test in progress for over 10 years, the effects of compositions consisting of vitamins and mineral additives have not been demonstrated yet (Kassof et al. 2001).

An ideal solution is to facilitate the transport ability of the Bruch's membrane, allowing all of the nutrients that are present in plasma to be provided.

As a result of intensive efforts to develop a treatment method capable of addressing the fundamental reason for age-related eye dysfunction including AMD, the inventors of this application found effects of a sea cucumber extract improvement in the transport ability of the Bruch's membrane and regeneration of the Bruch's membrane by a sea cucumber extract, and confirmed that the sea cucumber extract is able to be used as a composition for preventing and treating a Bruch's membrane dysfunction-associated disease. Therefore, the present invention was completed.

REFERENCES

[1] Birkedal-Hansen H, Moore W G, Bodden M K, Windsor L J, Birkedal-Hansen B, DeCarlo A, Engler J A. (1993) Matrix metalloproteinases: a review. Crit. Rev. Oral Biol. Med. 4:197-250.
[2] Handa J T, Verzijl N, Matsunaga H, Aotaki-Keen A, Lutty G A, to Koppele J M, Miyata T and Hjelmeland L M. Increase in the advanced glycation end-product pentosidine in Bruch's membrane with age. Invest. Ophthalmol. Vis. Sci. 1999; 40: 775-779.
[3] Holz F G; Sheraidah G S, Pauleikhoff D and Bird A C. Analysis of lipid deposits extracted from human macular and peripheral Bruch's membrane. Arch. Ophthalmol. 1994; 112: 402-406.
[4] Hussain A A, Lee Y, Zhang J J, Marshall J. (2011) Disturbed matrix metalloproteinase activity of Bruch's membrane in age-related macular degeneration (AMD). Invest. Ophthalmol. Vis. Sci. 52:4459-66.
[5] Hussain A A, Starita C, Hodgetts A, Marshall J. (2010) Macromolecular characteristics of ageing human Bruch's membrane: implications for age-related macular degeneration (AMD). Exp. Eye Res. 90:703-710.
[6] Hussain A A, Lee Y, Marshall J. (2010) High molecular weight gelatinase species of human Bruch's membrane: compositional analyses and age-related changes. Invest. Ophthalmol. Vis. Sci. 51:2363-71.
[7] Hussain A A, Starita C, and Marshall J. (2004) Chapter IV. Transport characteristics of ageing human Bruch's membrane: Implications for AMD. In: Focus on Macular Degeneration Research, (Editor O. R. Ioseliani). Pages 59-113. Nova Science Publishers, Inc. New York.
[8] Hussain A A, Rowe L, Marshall J. (2002) Age-related alterations in the diffusional transport of amino acids across the human Bruch's-choroid complex. Journal of the Optical Society of America, A, Optics, Image Science, & 19(1): 166-72.
[9] Karwatowski W S S, Jefferies T E, Duance V C, Albon J, Bailey A J & Easty D L. Preparation of Bruch's membrane and analysis of the age-related changes in the structural collagens. (1995) Brit. J. Ophthalmol. 79: 944-952.
[10] Kassof A, Kassoff J, Buehler J, et al., A randomized, placebo-controlled, clinical trial of high dose supplementation with vitamins C and E, beta carotene, and zinc for age-related macular degeneration and vision loss: AREDS report No. 8. Arch Ophthalmol. 2001; 119:1417-36.
[11] Kumar A, El-Osta A, Hussain A A, Marshall J. (2010) Increased sequestration of matrix metalloproteinases in ageing human Bruch's membrane: implications for ECM turnover. Invest. Ophthalmol. Vis. Sci. 51:2664-70.
[12] Moore D J and Clover G M. The effect of age on the macromolecular permeability of human Bruch's membrane. Invest. Ophthalmol. Vis. Sci. 2001; 42: 2970-2975.
[13] Moore D J, Hussain A A, Marshall J. (1995). Age-related variation in the hydraulic conductivity of Bruch's membrane. Invest. Ophthalmol. Vis. Sci. 36(7): 1290-7.
[14] Owsley C, Jackson G R, White M, Feist R and Edwards D. Delays in rod mediated dark adaptation in early age-related maculopathy. Ophthalmol. 2001; 108: 1196-1202.
[15] Owsley C, McGwin Jackson G R, Heinburger D C, Piyathilake C J, Klein R, White M F, Kallies K. Effect of short term, high-dose retinol on dark adaptation in age and age-related maculopathy. Invest. Ophthalmol. Vis. Sci. 2006. 47(4):1310-8.
[16] Ramratten R S, van der Schaft T L, Mooy C M, de Bruijn W C, Mulder P G H and de Jong P T V M. Morphometric analysis of Bruch's membrane, the choriocapillaris and the choroid in ageing. Invest. Ophthalmol. Vis. Sci. 1994; 35: 2857-2864.
[17] Starita C, Hussain A A, Pagliarini S, Marshall J. (1996) Hydrodynamics of ageing Bruch's membrane: implications for macular disease. Exp. Eye Res. 62(5): 565-72.
[18] Steinmetz R L, Haimovici R, Jubb C, Fitzke F W, Bird A. Symptomatic abnormalities of dark adaptation in patients with age-related Bruch's membrane change. Br. J. Ophthalmol. 1993; 77:549-554.
[19] Hussain A A, Lee Y (2016) unpublished data
[20] Lee Y, Hussain A A, Seok J, Kim S, Marshall J. (2015). Modulating the Transport Characteristics of Bruch's Membrane With Steroidal Glycosides and its Relevance to Age-Related Macular Degeneration (AMD). Invest. Ophthalmol. Vis. Sci. 56(13): 8403-18.

DISCLOSURE

Technical Problem

The present invention is directed to providing a pharmaceutical composition for preventing, delaying and treating a Bruch's membrane dysfunction-associated disease, which contains an extract or fraction of sea cucumber as an active ingredient.

The present invention is also directed to providing a health functional food composition for preventing, delaying and treating a Bruch's membrane dysfunction-associated disease, which contains an extract or fraction of sea cucumber as an active ingredient.

The present invention is also directed to providing a pharmaceutical composition for preventing, delaying and treating a Bruch's membrane dysfunction-associated disease, which contains Frondoside A, an isomer thereof, a hydrate thereof or a salt thereof as an active ingredient.

The present invention is also directed to providing a health functional food composition for preventing, delaying and treating a Bruch's membrane dysfunction-associated disease, which contains Frondoside A, an isomer thereof, a hydrate thereof or a salt thereof as an active ingredient.

Technical Solution

To attain the above-described objects, the present invention provides a pharmaceutical composition for preventing, delaying and treating a Bruch's membrane dysfunction-associated disease, which contains an extract or fraction of sea cucumber as an active ingredient.

The term "sea cucumber" used herein refers to a marine invertebrate belonging to the Class Holothuroidea and the Phylum Echinodermata, and includes *Psolus squamatus, Lipotrapeza japonica, Sclerodactyla multipes, Cucumaria, Plesiocolochirus inornatus*, etc., which belong to the Order Dendrochirotacea, *Apostichopus japonicus, Holothuria monacaria, Holothuria argus, Holothuria manacaria*, etc., which belong to the Order Aspidochirotida, Synaptidae, *Polycheira rufescens*, etc., which belong to the Order Apodida, *Paracaudina chilensis, Molpadia oolitica*, etc., which belong to the Order Molpadida, but the present invention is not limited thereto. The sea cucumber is recommended for use as tonics for promoting strength, medicines for a pregnant woman and an infirm woman, a health food for hypertension, arteriosclerosis, a diabetic patient and an obese patient, but no effect on age-related eye diseases has been known.

The term "extract" used herein includes an extract obtained by extracting sea cucumber, a dried product obtained by drying sea cucumber, a diluent or concentrate of the extract, a dried product obtained by drying the extract, a partially purified component or purified component of the extract, or a mixture thereof, a liquid extract, and all forms of extracts that can be formed using the liquid extract itself. The extract or fraction of the present invention may be preferably used in the form of a liquid after extraction.

In the sea cucumber extract of the present invention, the method of extracting the sea cucumber is not particularly limited, and thus an extraction method conventionally used in the art may be used. Non-limiting examples of the extraction methods may include hot water extraction, ultrasonic extraction, filtration, reflux extraction, etc., which may be used independently, or in combination of two or more thereof.

In the present invention, a type of an extraction solvent used to extract the sea cucumber is not particularly limited, and thus any solvent known in the art may be used. Non-limiting examples of the extraction solvents may include water, an alcohol, and a mixed solvent thereof, and as a solvent, preferably, a C1 to C4 alcohol, more preferably, a C1 to C2 low alcohol, and even more preferably, an 80% ethanol aqueous solution may be used, but the present invention is not limited thereto. The sea cucumber extract of the present invention is preferably water or an ethanol extract.

In the present invention, when the extraction of the sea cucumber is performed by hot water extraction, the sea cucumber is preferably extracted 1 to 5 times, and more preferably 3 times, but the present invention is not limited thereto. The extraction solvent may be added at 0.1- to 100-fold, and preferably 0.3- to 5-fold the dry sea cucumber weight. An extraction temperature is preferably 20 to 130° C., but the present invention is not limited thereto. In addition, an extraction time is preferably 30 minutes to 48 hours, but the present invention is not limited thereto.

In a method of preparing the sea cucumber extract, preferably, vacuum evaporation is performed using a vacuum concentrator or a rotary vacuum evaporator, but the present invention is not limited thereto. In addition, drying is performed by decompression drying, vacuum drying, boiling drying, spray drying, or freeze drying, but the present invention is not limited thereto.

Although a method of preparing the dried product of sea cucumber may be natural drying, hot-air drying or freeze drying, any method known in the art for removing moisture from the sea cucumber is used without limitation.

In the method of extracting or drying sea cucumber according to the present invention, the outer coat and the internal organs of the sea cucumber may be entirely or separately extracted or dried, and the extract or dried product of the outer coat or the internal organs may be used individually or in combination thereof.

According to an exemplary embodiment of the present invention, an extract may be obtained by preparing a sea cucumber powder by grinding dried sea cucumber, adding 70% ethanol as an extraction solvent to the sea cucumber powder to perform extraction for about 3 to 6 hours, and removing the ethanol under a vacuum condition.

The term "fraction" used herein refers to a product obtained by performing fractionation to isolate a specific component or specific component group from a mixture including various components.

A fractionation method for obtaining the fraction in the present invention is not particularly limited, and thus a method conventionally used in the art may be used. A non-limiting example of the fractionation method may include a method of obtaining a fraction from the extract by treating an extract obtained by extracting sea cucumber with a predetermined solvent.

In the present invention, a type of a fractionation solvent used to obtain the fraction is not particularly limited, and thus any solvent known in the art may be used. Non-limiting examples of the fractionation solvents may include polar solvents such as water, an alcohol, etc.; and non-polar solvents such as hexane, ethyl acetate, chloroform, and dichloromethane, etc. These may be used alone, or in combination of two or more thereof. Among the fractionation solvents, a C1 to C4 alcohol is preferably used.

Since an active ingredient of the present invention improves the transport function of the Bruch's membrane, it is effective in preventing the occurrence of a Bruch's membrane dysfunction-associated disease, delaying the progression of the disease, or treating the disease.

The active ingredient of the present invention may improve the hydraulic conductivity of the Bruch's membrane, improve the material diffusion function of the Bruch's membrane, or remove proteins or lipids bound to or trapped in the Bruch's membrane, thereby improving the transport function.

The active ingredient of the present invention is effective in preventing the occurrence of a Bruch's membrane dysfunction-associated disease, delaying the progression of the diseases or treating the disease by regenerating the Bruch's membrane and improving the functions of the Bruch's membrane.

The active ingredient of the present invention may regenerate the Bruch's membrane and improve the functions thereof by removing a high molecular weight (HMW) complex or a lipid component, which is bound to or deposited on the Bruch's membrane.

In addition, the active ingredient of the present invention may regenerate the Bruch's membrane and improve the functions thereof by secreting pro-MMP2, pro-MMP9, active MMP2 and active MMP9 from the matrix of the Bruch's membrane.

In addition, the active ingredient of the present invention may regenerate the Bruch's membrane and improve the functions thereof by activating the secretion of active MMPs from RPE cells.

As described above, the sea cucumber extract composition of the present invention helps to decompose materials which are polymerized in the Bruch's membrane, thereby aging the Bruch's membrane and allowing the functions thereof to be lost, and to supply nutrients to the eyes and discharge waste by secreting nutrients such as proteins or lipids trapped in or bound to the matrix of the Bruch's membrane and waste. In addition, as the sea cucumber extract composition of the present invention allows the recovery of the function of an enzyme by secreting MMPs of the Bruch's membrane, it is involved in regenerating the functions of the Bruch's membrane, and increases the hydraulic conductivity and material diffusion of the eyes, resulting in prevention of retinal aging, and an effect of preventing, delaying and treating the age-related loss of retinal functions by regenerating the retinal functions.

The term "prevention" or "delay" used herein refers to all actions involved in inhibiting or delaying the occurrence of a disease occurring due to Bruch's membrane dysfunction by administering the composition of the present invention to a subject.

The term "treatment" used herein refers to all actions involved in alleviating or beneficially changing symptoms of a disease occurring by Bruch's membrane dysfunction by administering the composition of the present invention to a subject.

The term "improvement" used herein refer to all actions involved in at least reducing parameters related to conditions being treated, for example, the severity of symptoms.

In the pharmaceutical composition of the present invention, the sea cucumber extract or a fraction thereof is preferably contained at 0.1 to 99.99 wt %, more preferably, 10 to 99.99 wt %, and even more preferably, 50 to 99.99 wt % based on the total weight of the pharmaceutical composition. Within the above range, there is an advantage of being more suitable for achieving the objects of the present invention due to sufficient effects of the sea cucumber extract or a fraction thereof on improvement of the transport function of the Bruch's membrane, regeneration of the Bruch's membrane, and improvement of the functions of the Bruch's membrane.

The pharmaceutical composition of the present invention may contain the sea cucumber extract or a fraction thereof as an active ingredient, and further contain a pharmaceutically acceptable carrier.

In the present invention, the "pharmaceutically acceptable" means conventionally being used in the pharmaceutical field without irritating an organism when the composition is administered thereto and inhibiting the biological activity and characteristics of the administered compound.

The pharmaceutical composition of the present invention may be formulated with the carrier, and thus used in food, medicines, feed supplements, drinking water supplements, etc. In the present invention, a type of the carrier is not particularly limited, and any carrier conventionally used in the art is able to be used. Non-limiting examples of the carriers may include saline, distilled water, Ringer's solution, buffered saline, an albumin injection solution, lactose, dextrose, sucrose, sorbitol, mannitol, xylitol, erythritol, maltitol, maltodextrin, glycerol, ethanol, etc. These carriers may be used alone or in combination of two or more thereof.

In addition, the pharmaceutical composition of the present invention may be used by adding a pharmaceutically acceptable additive such as an excipient, a diluent, an antioxidant, a buffer or a bacteriostatic agent, if needed, and further adding a filler, a thickening agent, a wetting agent, a disintegrant, a dispersant, a surfactant, a binder or a lubricant.

The pharmaceutical composition of the present invention may be formulated in various forms suitable for oral or parenteral administration. Non-limiting examples of preparations for oral administration may include troches, lozenges, tablets, water-soluble suspensions, oil-soluble suspensions, formulated powder, granules, emulsions, hard capsules, soft capsules, syrups or elixirs.

To formulate the pharmaceutical composition of the present invention for oral administration, the composition may include a binder such as lactose, saccharose, sorbitol, mannitol, starch, amylopectin, cellulose or gelatin; an excipient such as dicalcium phosphate; a disintegrating agent such as corn starch or sweet potato starch; or a lubricant such as magnesium stearate, calcium stearate, sodium stearyl fumarate or polyethylene glycol wax, a sweetening agent, a flavoring agent, a syrup agent, etc.

Further, other than the above-described materials, as a capsuling agent, a liquid carrier such as fat oil may be further added.

Non-limiting examples of the parenteral preparations may include injections, suppositories, respiratory inhalation powder, an aerosol for spray, an ointment, an applicable powder, oil, a cream, etc.

To formulate the pharmaceutical composition of the present invention for parenteral administration, a sterilized aqueous solution, a non-aqueous solvent, a suspending agent, an emulsion, a freeze-dried preparation, or an external preparation may be used, and as the non-aqueous solvent or suspending agent, propylene glycol, polyethylene glycol, a vegetable oil such as olive oil, or an injectable ester such as ethyl oleate may be used.

In addition, more specifically, when the pharmaceutical composition of the present invention is formulated in the form of an injection fluid, the composition of the present invention may be mixed with a stabilizer or buffer in water, thereby preparing a solution or suspension, and the solution or suspension may be formulated in a unit dosage form such as an ampoule or vial. In addition, when the pharmaceutical composition of the present invention is formulated as an aerosol, it may be mixed with additives such as a propellant, etc. to disperse a water-diffused concentrate or wet powder.

In addition, when the pharmaceutical composition of the present invention is formulated in the form of an ointment or cream, an animal oil, a vegetable oil, wax, paraffin, starch, tragacanth, a cellulose derivative, polyethylene glycol, silicone, bentonite, silica, talc, or zinc oxide may be used as a carrier.

A pharmaceutically effective amount or effective dose of the pharmaceutical composition of the present invention may vary according to a formulation method, an administration method, an administration time and/or administration route of the pharmaceutical composition, and specifically, may vary according to various factors and similar factors well known in the medical field such as the type and degree of a reaction to be accomplished by administrating the pharmaceutical composition, the type, age, body weight and general health condition of a subject for administration, the symptoms or severity of a disease, sex, diet, excretion, components of a drug or other compositions used together for a corresponding subject at the same or different time, etc. Those of ordinary skill in the art may easily determine and prescribe an amount or dose effective for the desired treatment.

The dose of the pharmaceutical composition of the present invention for a more preferable effect is preferably 0.01 to 1,000 mg/kg, and more preferably, 1 to 500 mg/kg per day. The pharmaceutical composition of the present invention may be daily administered once, or divided into several doses. Therefore, the dose may not limit the scope of the present invention in any way.

The administration route and method of the pharmaceutical composition of the present invention may be independent of each other. The method is not particularly limited, and thus any administration route and method may be used as long as the pharmaceutical composition can reach a desired relevant site. The pharmaceutical composition may be orally or parenterally administered.

As parenteral administration, for example, intravenous administration, intraperitoneal administration, intravenous administration, transdermal administration or subcutaneous administration, application or spraying of the composition onto a diseased site or inhalation may be used, but the present invention is not limited thereto.

The pharmaceutical composition of the present invention is preferably administered orally or injected.

The composition of the present invention may further include Frondoside A to prevent and delay a Bruch's membrane dysfunction-associated disease, and increase a therapeutic effect thereof.

The "Frondoside A" used herein is a saponin compound represented by the following formula, and is known to be included in the sea cucumber of the present invention. Its CAS No. is 127367-76-4 (anhydrous), and its chemical formula is $C_{60}H_{96}O_{29}SNa$. In the present invention, it is confirmed that Frondoside A is involved in improving the hydraulic conductivity of the Bruch's membrane, improving the transport function of the Bruch's membrane through MMP and lipid secretion, regenerating the Bruch's membrane, and improving the functions thereof, and through this, a novel use of Frondoside A for preventing, delaying, treating and improving a Bruch's membrane dysfunction-associated disease was identified.

When the health functional food composition of the present invention is used as a food additive, it may be suitably used as is or in combination with a different food or food component according to a conventional method.

A type of the food is not particularly limited, and includes all types of food in a general sense. Non-limiting examples of food to which the material is added may include meat, sausage, bread, chocolate, candy, snacks, confectioneries, pizza, ramen, other noodles, gum, dairy products including ice cream, various soups, beverages, tea, drinks, alcoholic beverages and vitamin complexes.

When the health functional food composition of the present invention is a beverage composition, like a general beverage, various flavors or natural carbohydrates may be contained as additional components. Non-limiting examples of the natural carbohydrates may include monosaccharides such as glucose, fructose, etc.; disaccharides such as maltose, sucrose, etc.; natural sweetening agents such as dextrin, cyclodextrin, etc.; and synthetic sweeteners such as saccharin and aspartame. The proportion of the additional component added may be suitably determined by one of ordinary skill in the art.

[Chemical Formula]

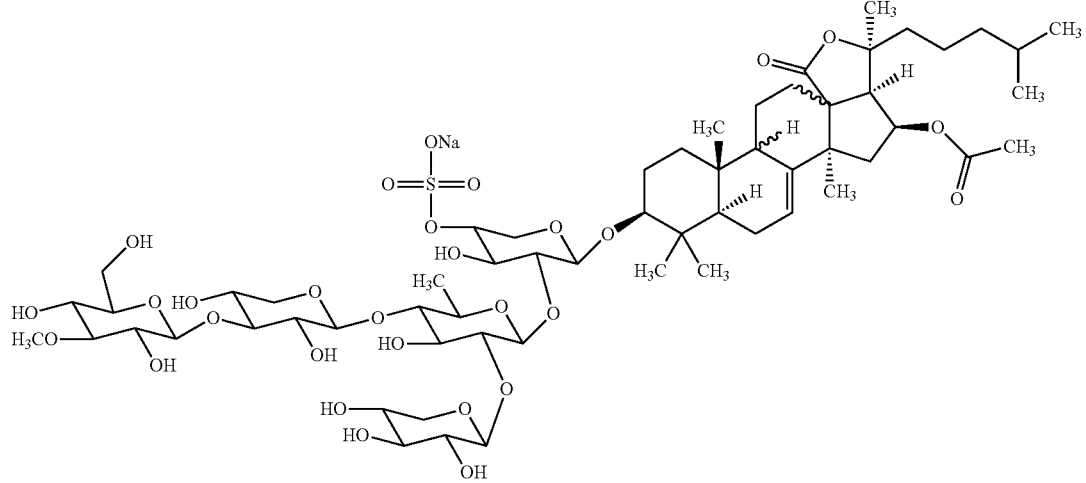

The composition of the present invention may further include one or more compositions selected from the group consisting of amino acids, antioxidant materials, minerals, metallic materials, lutein, astaxanthin and zeaxanthin to prevent and delay a Bruch's membrane dysfunction-associated disease, and increase a therapeutic effect thereof.

In the present invention, the Bruch's membrane dysfunction-associated disease may be AMD, Sorsby's fundus dystrophy, Malattia Levintanese (ML), Stargardt disease, Best's vitelliform retinal dystrophy or Doyne's honeycomb retinal dystrophy (DHRD), but the present invention is not limited thereto.

In addition, the present invention provides a health functional food composition for preventing, delaying and treating a Bruch's membrane dysfunction-associated disease, which contains the sea cucumber extract as an active ingredient.

In the health functional food composition of the present invention, the sea cucumber extract or a fraction thereof, and an efficacy thereof is the same as described above in connection with the pharmaceutical composition of the present invention.

Other than these, the health functional food composition of the present invention may contain a variety of nutrients, vitamins, electrolytes, flavoring agents, coloring agents, pectic acid and a salt thereof, alginic acid and a salt thereof, an organic acid, a protective colloid thickening agent, a pH adjuster, a stabilizer, a preservative, glycerin, an alcohol, or a carbonating agent used in carbonated beverages. Other than these, the health functional food composition of the present invention may contain fruit pulp for preparing natural fruit juices, fruit drinks or vegetable drinks. These components may be used independently or in combination of two or more thereof. The proportions of these additives may also be suitably selected by one of ordinary skill in the art.

In addition, the present invention provides a pharmaceutical composition for preventing, delaying and treating/improving a Bruch's membrane dysfunction-associated disease, which includes Frondoside A, an isomer thereof, a hydrate thereof or a salt thereof as an active ingredient.

In addition, the present invention provides a health functional food composition for preventing, delaying and treating a Bruch's membrane dysfunction-associated disease, which includes Frondoside A, an isomer thereof, a hydrate thereof or a salt thereof as an active ingredient.

Advantageous Effects

A composition according to the present invention is effective in improving the transport function of the Bruch's membrane, and delaying or restoring the aging of eyes by stimulating the regeneration of the Bruch's membrane, and can also have excellent efficacy in preventing and treating a disease such as AMD occurring due to age-related Bruch's membrane dysfunction, Sorsby's fundus dystrophy, ML, Stargardt disease, Best's vitelliform retinal dystrophy or DHRD.

MODES OF THE INVENTION

The present invention will be described in further detail as follows.

Age-related degenerative changes in the transport function of the Bruch's membrane cause vision impairment in the elderly, and in severe cases, cause AMD leading to blindness.

Numerous studies have shown that aging has a seriously adverse effect on the material transport capacity of the Bruch's membrane and the process of removing waste (Hussain et al., 2002; 2004; 2010; Starita et al. 1996; Moore et al. 1995; Moore and Clover, 2001), and it has been known that waste accumulated in the Bruch's membrane increased in thickness due to aging consists of lipids and denatured proteins. Moreover, it has been known that the fundamental reason for the accumulation of waste present in the Bruch's membrane is an insufficient role of proteases called matrix metalloproteinases (MMPs) in regeneration of the Bruch's membrane.

An MMP is a protease, which is secreted into the Bruch's membrane from RPE in a pro-form, which is an inactivated state. As a small peptide is removed from this pro-form, MMPs are transformed into activated forms, which are active MMP2 and active MMP9. According to activation, the activated MMP2 and MMP9 enzymes are able to decompose most of the materials constituting the extracellular matrix, and removes a damaged component and replaces it with a new material. According to the mechanism of regeneration of the Bruch's membrane, the structure and functions of the Bruch's membrane may be maintained in a healthy condition. However, it has been known that, due to the aging of the Bruch's membrane, amounts of the activated forms of MMP2 and MMP9 are reduced, and in the Bruch's membrane of a macular degeneration patient, the amounts of activated MMP2 and MMP9 are decreased by about 60%, compared to the average in a similar age group (Hussain et al., 2011).

Figure 1:
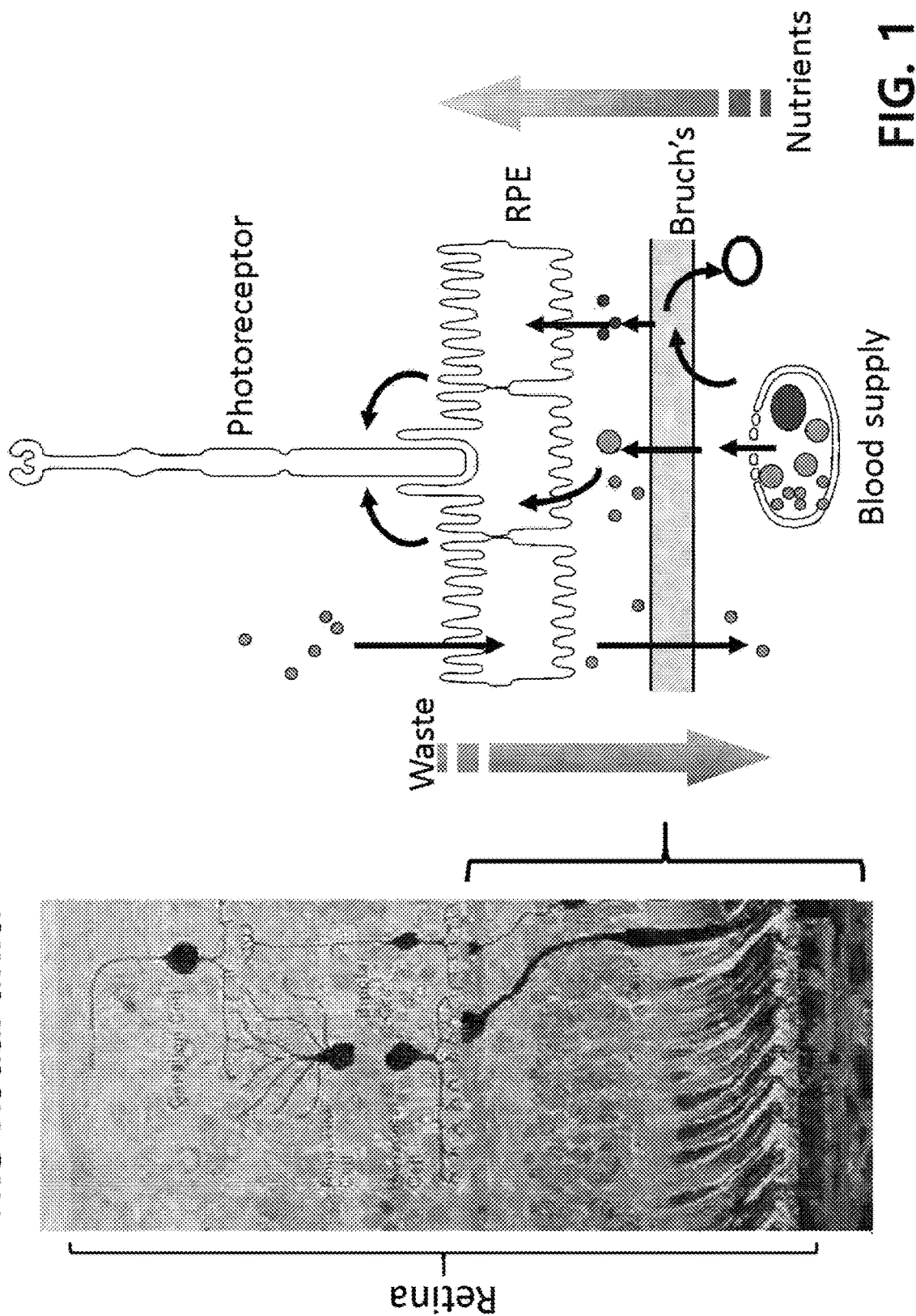
FIG. 1 is a cross-sectional image of a human retina and a diagram illustrating components of phototransduction.
Figure 2:
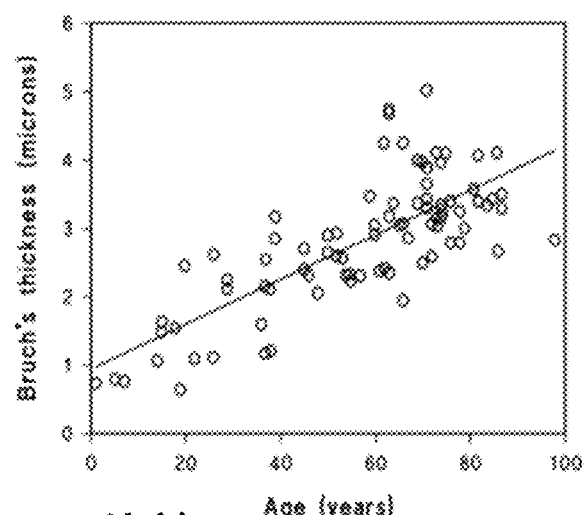
FIG. 2 is a set of graphs showing age-related structural changes of the Bruch's membrane, in which, as aging progresses, (A) the thickness of the Bruch's membrane increases 2- to 3-fold, (B) the accumulative amount of damaged or denatured collagen increases, (C) a major lipid material such as a cholesterol ester increases exponentially, and (D) protein aggregation occurs due to reduction of free thiol groups.
Figure 2:
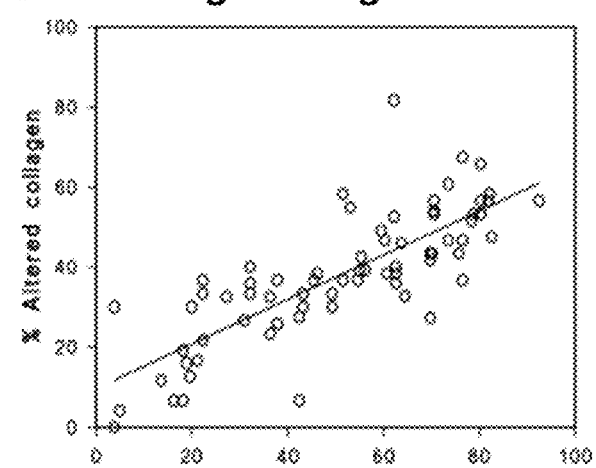
Figure 2:
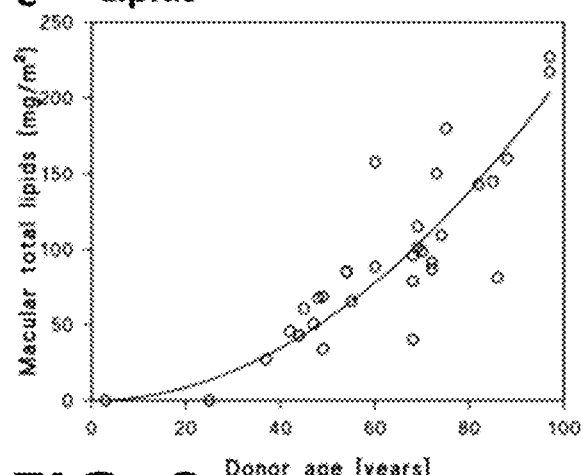
Figure 2:
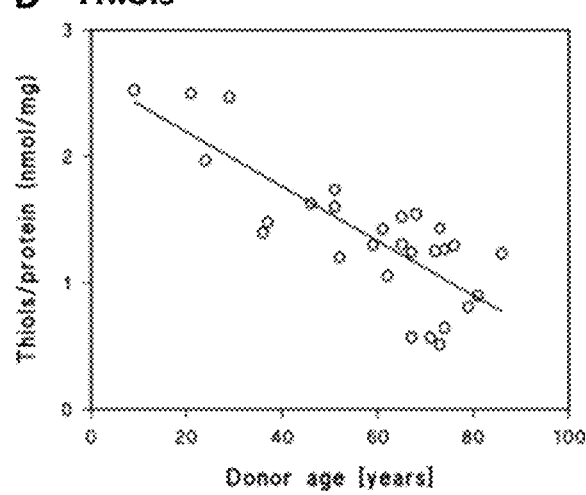
Figure 3:
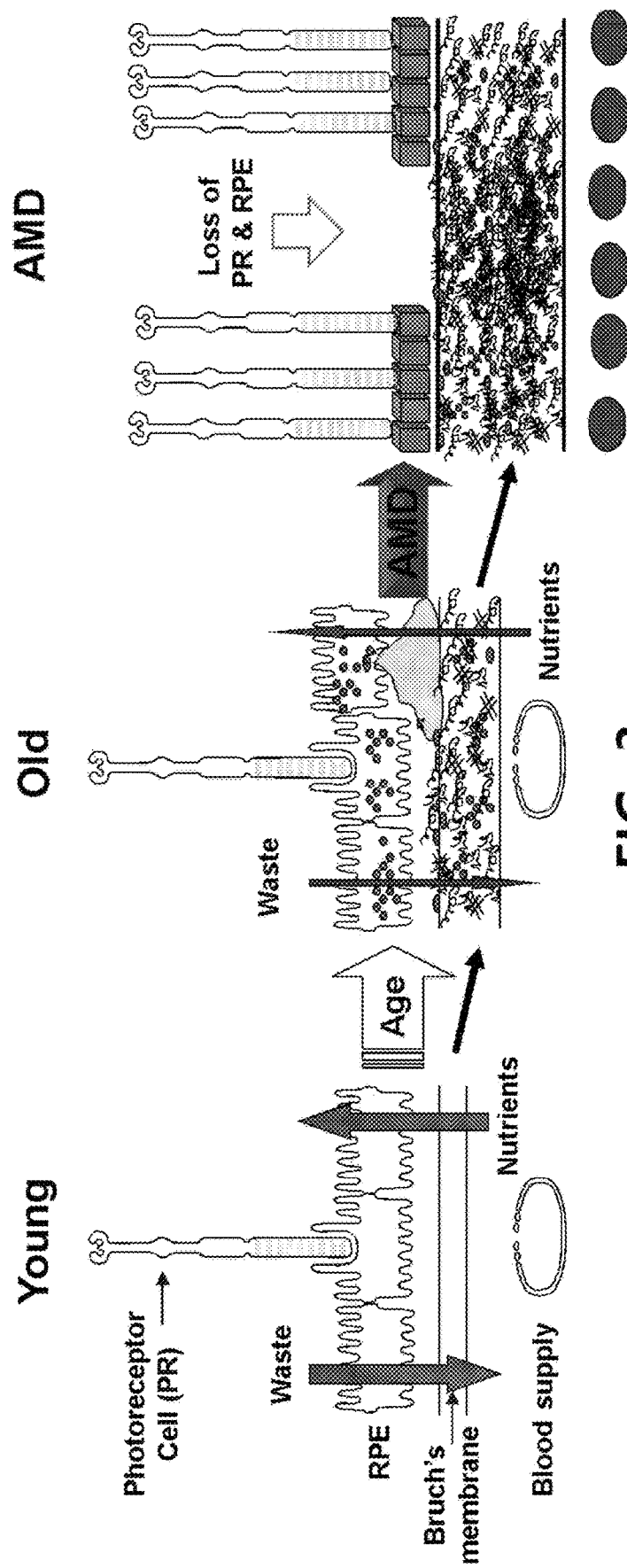
FIG. 3 is a diagram illustrating an age-related change of the Bruch's membrane and a drastic change in a macular degeneration patient.
Figure 4:
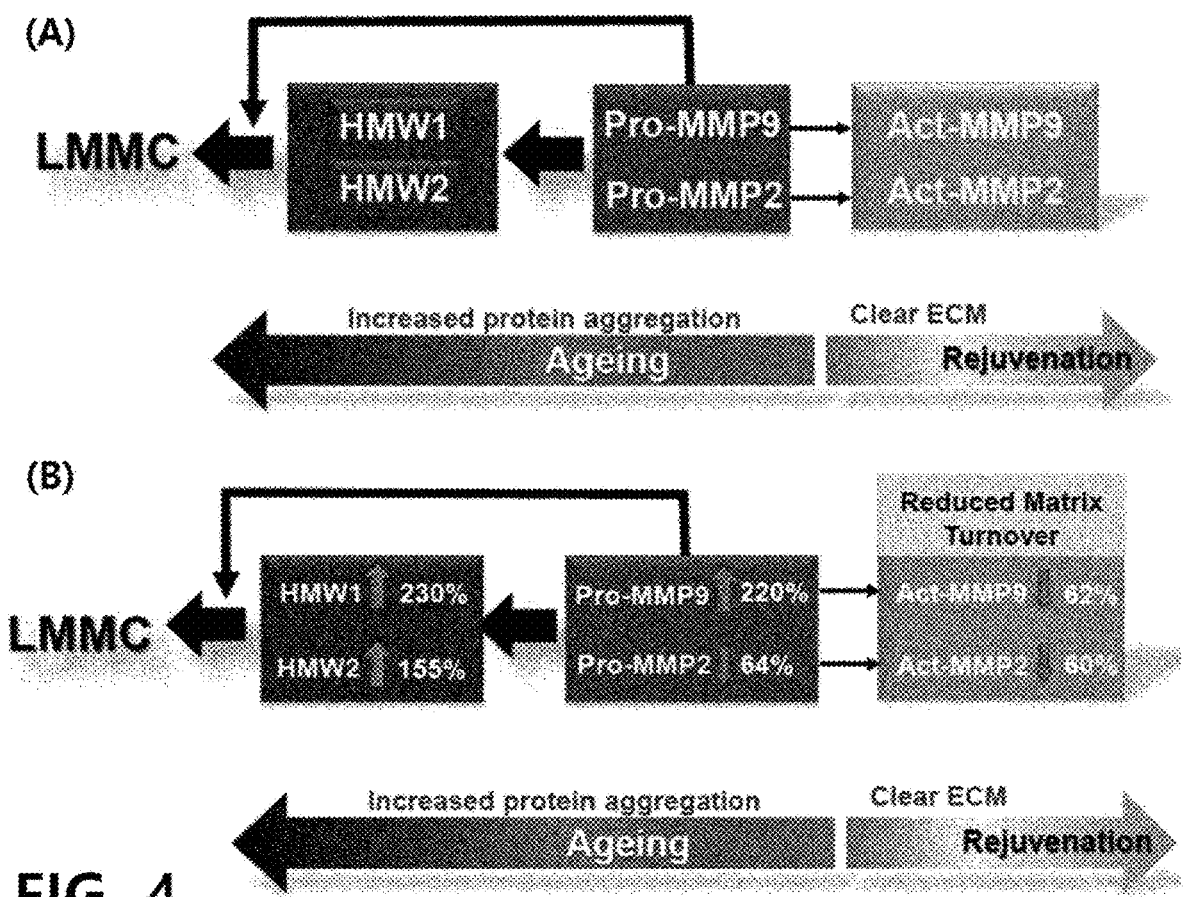
FIG. 4 shows the action mechanism of MMPs involved in aging and regeneration of the Bruch's membrane and an abnormal MMP action mechanism in a macular degeneration patient.

Specifically, the age-related MMP action mechanism is shown in FIG. 4. pro-MMP2 and pro-MMP9, which are pro-forms, form polymer compounds called HMW1 and HMW2 (HMW complexes) in the Bruch's membrane. In addition, these materials are combined with different pro-MMP2 and pro-MMP9 molecules to form even larger high molecular weight materials, called large macromolecular complexes (LMMCs) (Kumar et al., Hussain et al. 2010). When the synthesis of such high molecular weight materials is increased due to aging, the polymeric compounds are trapped in or bound to the matrix, pro-MMP and active MMP are also trapped in the membrane and cannot be used. Therefore, since the amount of free MMPs required for the regeneration of the Bruch's membrane is reduced, the decomposition and regeneration of the membrane are not normally performed, resulting in the accumulation of a considerable amount of waste and reduction in the transport capacity of the membrane.

To identify an age-related change in the transport function of the Bruch's membrane, the macular regions involved in central vision and the peripheral regions are separated from the eyes of 56 normal persons and 11 macular degeneration patients ranging from 1 to 96 years of age, and the effect of the transport function change on these regions are evaluated.

Figure 5:
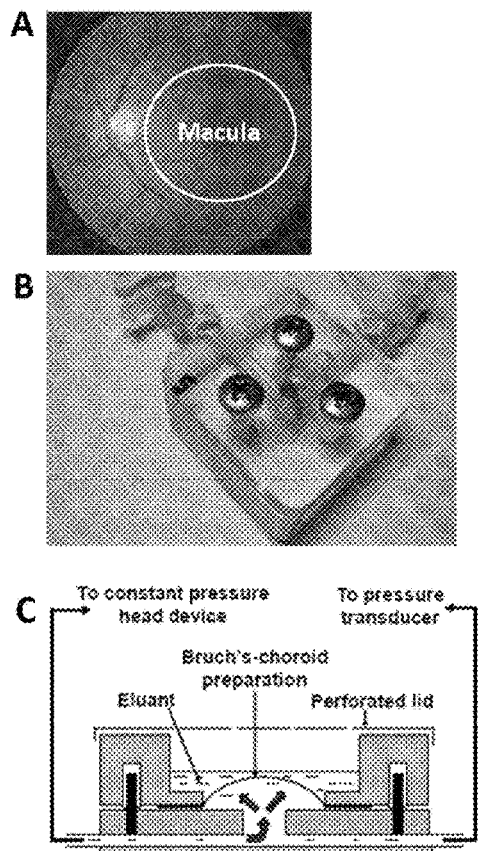
FIG. 5 shows results of changes in age-related hydraulic conductivity of the human Bruch's membrane in a normal person and a macular degeneration patient.

First, to confirm the waste transport ability, the hydraulic conductivity of the Bruch's membrane isolated from a donated eye was measured. The isolated Bruch's membrane was mounted in an open-type Ussing chamber to measure a quantitative change in fluid under hydrostatic pressure and calculate a change in hydraulic conductivity (FIGS. 5B and 5C). As a result, it can be seen that the fluid transport ability of the macular region is exponentially decreased as aging progresses, and the transport ability is halved every 16 years (FIG. 5D). The data of FIG. 5D is expressed using a semi-log plot with the logarithmic scale on the y-axis to convert exponential decay to a linear plot. To maintain the function of photoreceptor cells, the Bruch's membrane requires a minimal hydraulic conductivity function, which represents a failure line. When the transport function goes below the failure line, fluid accumulation below the RPE results in RPE detachment, and the death of overlying photoreceptor cells. These symptoms are shown in about 12 to 20% of macular degeneration patients. In the case of normal persons, this line does not go below the failure threshold, but even in a normal elderly population, the line may cross the failure threshold, and in this case, serious problems such as abnormal night vision occur. Since the macular region of a macular degeneration patient is considerably damaged due to the nature of this disease, it is impossible to independently measure only the macular region. The hydraulic conductivity of the peripheral region is also exponentially decreased in a similar pattern as the macular region, and the half-life of the function is about 22 years (FIG. 5E). All of the hydraulic conductivities measured for the peripheral regions of the 11 macular degeneration patients may be observed to be below the mean regression line (refer to the black circle and the red line in FIG. 5E), showing that, in the peripheral region, rather than the macular region, the decrease in the material transport function progresses to a serious condition.

Figure 6:
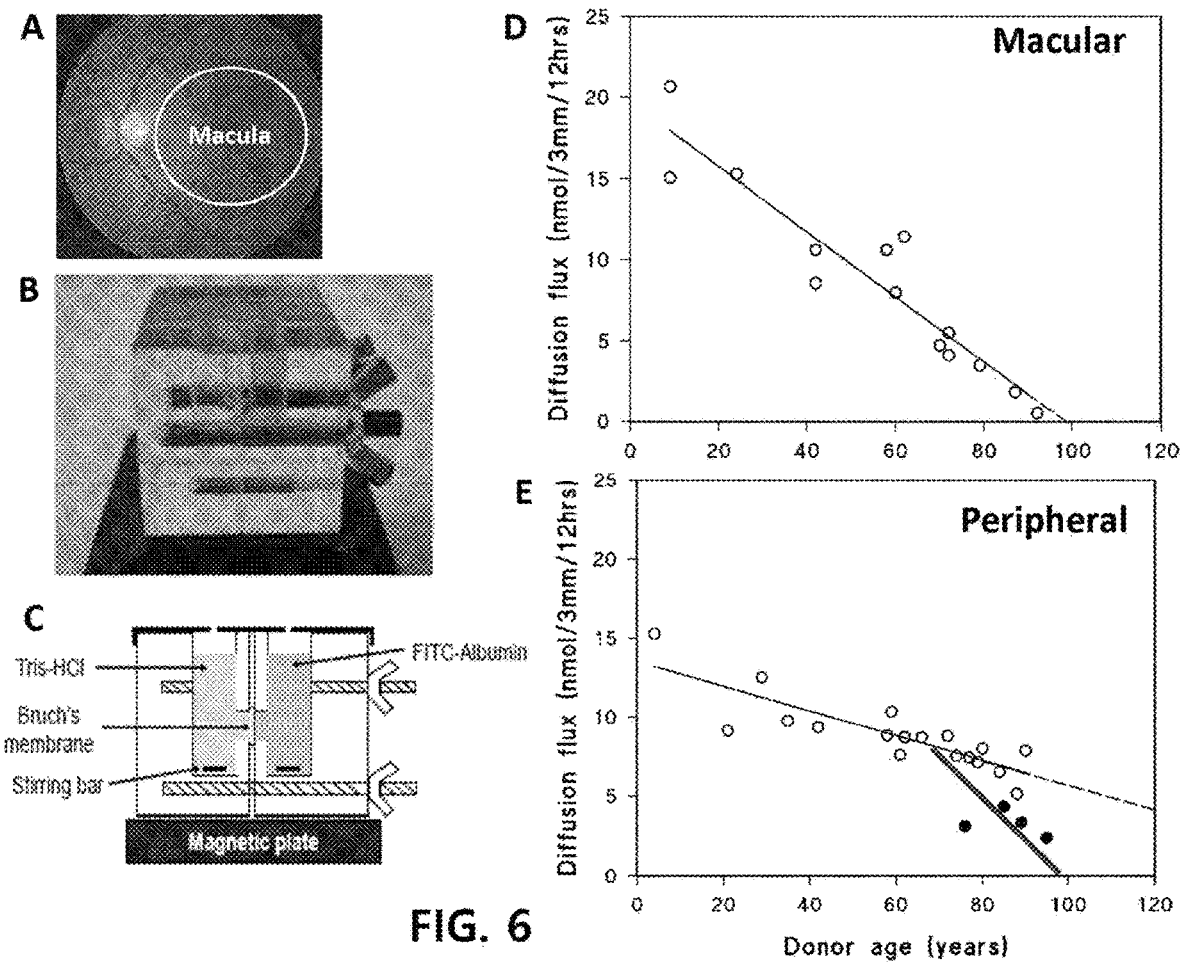
FIG. 6 shows results of age-related diffusion changes of the human Bruch's membrane in a normal person and a macular degeneration patient.

Subsequently, to confirm the nutrient transport ability of the Bruch's membrane, a protein diffusion experiment is performed. Specifically, the experiment is performed by diffusion of FITC-dextran (MW 23 kDa) through the Bruch's membrane using a general Ussing chamber (FIGS. 6B and 6C). Dextran is selected as a material having a similar size to most carrier proteins involved in transporting materials such as vitamin A, trace metals, lipids, etc. It can be confirmed that, due to aging of the Bruch's membrane, the diffusion of a protein-sized material passing through the macular region is rapidly decreased (FIG. 6D). For this reason, although there is a normal level of vitamins or antioxidant materials in the plasma, a deficiency of these materials is observed in the macular region. In the peripheral region, compared with the macular region, the decline in diffusion is slower (FIG. 6E), but it is confirmed that diffusion is very rapidly decreased in the case of a macular degeneration patient (see the black circle and the red line in FIG. 6E). As described above, compared with the decrease in the peripheral region, if the function of the macular region in a macular degeneration patient can be measured, it can be confirmed that the decrease can progress much faster and more drastically than that of the peripheral region. The decrease in diffusion transport interferes with nutrient supply and the removal of harmful waste, which in turn increases the risk of damage and death of RPE and photoreceptor cells and leads to death.

Hereinafter, the present invention will be described in further detail with reference to examples. The examples are merely provided to more fully describe the present invention, and it will be obvious to those of ordinary skill in the art that the scope of the present invention is not limited to the following examples.

Example 1. Preparation of Sea Cucumber Extract

Dried sea cucumber was ground using a grinder, thereby preparing sea cucumber powder, 70% ethanol was added thereto, and then extraction was performed for about 3 to 6 hours. The ethanol was removed under a vacuum condition, thereby preparing a sea cucumber extract used in the example of the present invention.

Example 2. Effect of Sea Cucumber Extract on Improvement of Hydraulic Conductivity of Bruch's Membrane To confirm the effect of the sea cucumber extract prepared in Example 1 on the hydraulic conductivity of the Bruch's membrane, the eyes of 14 ocular donors (52 to 84 years old) were used for the experiment. Specifically, the Bruch's membrane isolated from the eye of a donor was incubated with a 2.5% sea cucumber extract for 24 hours, and Tris-HCl was used as a control.

Figure 7:
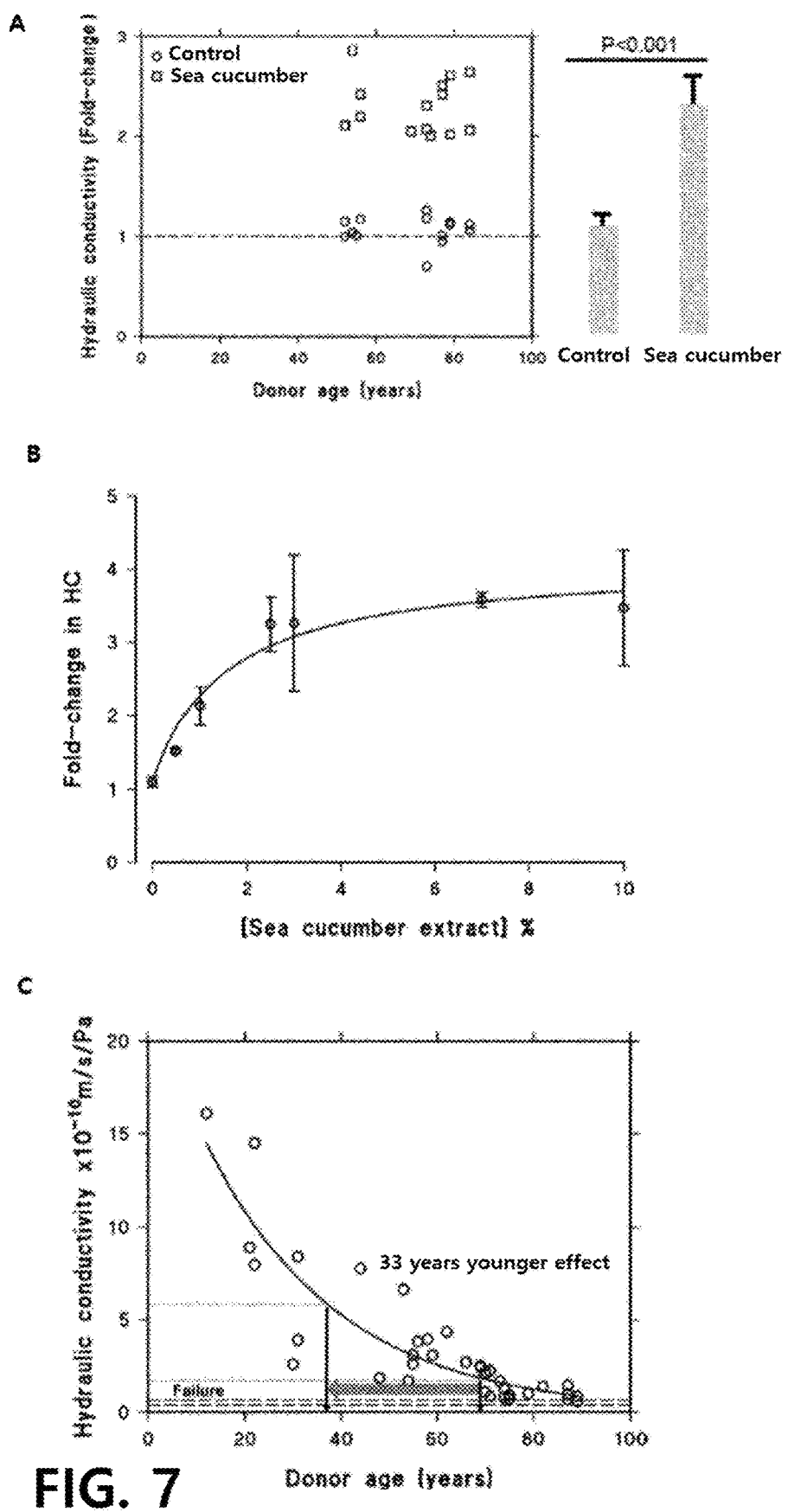
FIG. 7 shows the effect of a sea cucumber extract of the present invention on improvement of the transport function of the Bruch's membrane.

The result is shown in FIG. 7, and it can be seen that the hydraulic conductivity of the Bruch's membrane was increased 2.3-fold by the sea cucumber extract (FIG. 7A, p<0.001). The hydraulic conductivity-improving effect of the sea cucumber extract is the same as the effect of making the Bruch's membrane about 20 to 25 years younger. Due to such improvement of hydraulic conductivity, the Bruch's membrane does not reach the failure threshold, and therefore, the probability of developing macular degeneration is lowered.

In addition, to investigate the improvement of the transport function of the Bruch's membrane according to the dose of the sea cucumber extract, Bruch's membranes isolated from the eyes of four donors ranging from 69 to 84 years of age were measured, a dose response curve for the improvement of hydraulic conductivity was expressed. Specifically, the Bruch's membrane was mounted in an open-type Ussing chamber, Tris-HCl buffer was passed through a tube under hydrostatic pressure, and then after a certain period of time, the solution passing through the tube was taken to measure fluid transport. In the control, only Tris-HCl was used, and in the experimental groups, 0 to 10% sea cucumber extracts were treated. After incubation for 24 hours, fluid transport was measured again ([13] Moore D J, Hussain A A, Marshall J. (1995). Age-related variation in the hydraulic conductivity of Bruch's membrane. Invest. Ophthalmol. Vis. Sci. 36(7): 1290-7. [17] Starita C, Hussain A A, Pagliarini S, Marshall J. (1996) Hydrodynamics of ageing Bruch's membrane: implications for macular disease. Exp. Eye Res. 62(5): 565-72.)

As a result, according to the dose response curve of the sea cucumber extract shown in FIG. 7, as the dose of the sea cucumber extract increased, the hydraulic conductivity of the membrane was improved, and the hydraulic conductivity in a saturated state increased 3.2-fold, compared with when the sea cucumber extract was not added (FIG. 7B), which means that the hydraulic conductivity function was improved to be about 33 years younger in the age-related reduction curve (FIG. 7C).

Therefore, it was confirmed that the sea cucumber extract can have a significant influence on the improvement in the transport function of the Bruch's membrane in various age ranges in which aging progresses.

Example 3. Effect of Sea Cucumber Extract on Removal of Lipid Waste of Bruch's Membrane The major components of the lipid waste of the Bruch's membrane are cholesterol esters, cholesterols, triglycerides, and phospholipids. To confirm whether the sea cucumber extract is effective in removing a lipid extract accumulated in the Bruch's membrane, a dose-response experiment was performed. In detail, Bruch's membranes isolated from the eyes of four persons (50 to 82 years old) were suspended in Tris-HCl buffer and homogenized. A homogenate was centrifuged to be separated into a supernatant and a pellet containing lipid waste. The pellet was mixed again with Tris-HCl buffer, and incubated with 0~2.5% sea cucumber extracts in a 37° C. incubator for 24 hours. After the incubation, the sample was centrifuged to obtain a pellet, and an amount of lipid secreted into a supernatant from the pellet was quantified by thin layer chromatography (TLC).

Figure 8:
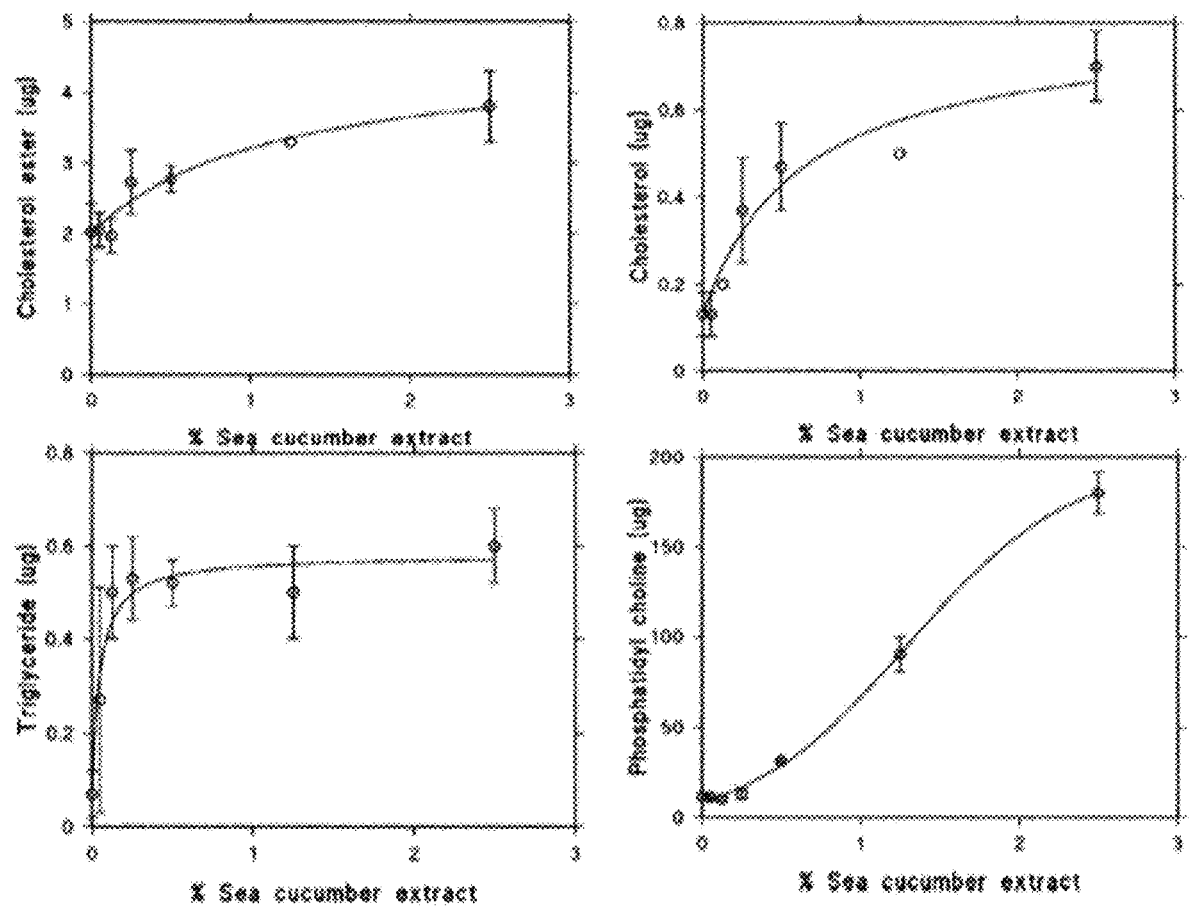
FIG. 8 is a dose response curve exhibiting the effect of a sea cucumber extract of the present invention on the secretion of a lipid from the Bruch's membrane.

As a result, secretion data and kinetics of various types of lipids were obtained. As shown in FIG. 8, it was confirmed that the secretion of cholesterol esters, cholesterols and triglycerides showed hyperbolic kinetic behavior, and the secretion of phosphatidylcholine showed sigmoid kinetic behavior, and when being incubated with the sea cucumber extract, the lipid waste deposited in the Bruch's membrane was diffused and secreted from the membrane.

Example 4. Effect of Sea Cucumber Extract on MMP Enzyme Secretion of Bruch's Membrane The MMP enzyme of the Bruch's membrane is present while being free or bound to the membrane. To confirm whether the sea cucumber extract can remove the MMP enzyme from the Bruch's membrane, first, membrane-binding MMPs were confirmed in the isolated Bruch's membrane.

Figure 9:
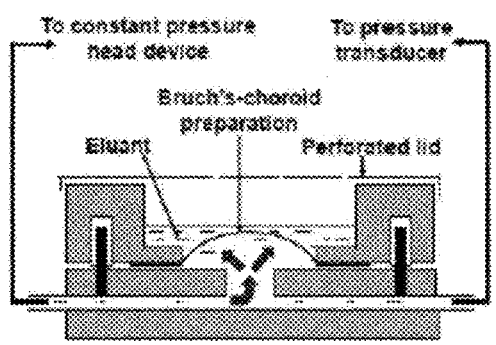
FIG. 9 shows the result of removing a free MMP enzyme from a human Bruch's membrane.
Figure 9:
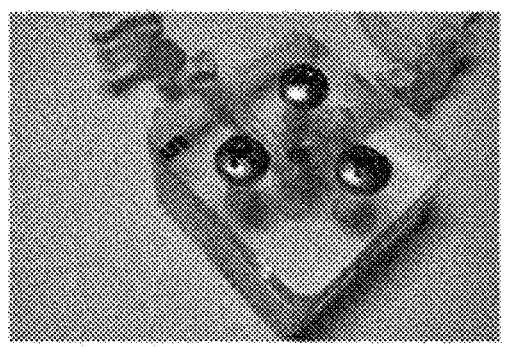
Figure 9:
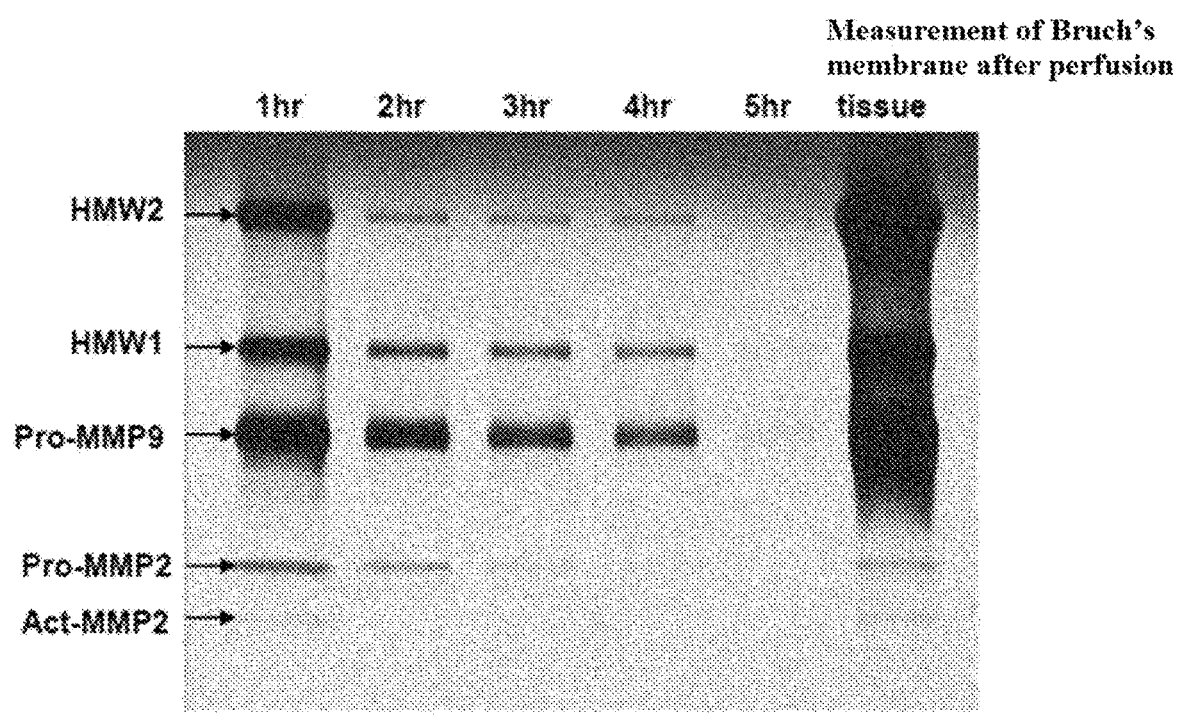

When the isolated Bruch's membrane was mounted in a Ussing chamber and perfused with Tris-HCl buffer, free MMPs were slowly secreted from the Bruch's membrane for about 6 to 12 hours according to the hydraulic conductivity of the Bruch's membrane (FIG. 9A). After free MMPs were secreted from the membrane, the Bruch's membrane was separated from the chamber, and then MMPs remaining in the membrane were extracted using SDS buffer. In the case of soluble or free MMP components, most were slowly secreted between 5 to 12 hours of perfusion (FIG. 9B). However, most of the MMPs present in the Bruch's membrane are bound to or trapped in the membrane, and after 5 to 12 hours of the perfusion, it can be confirmed that MMPs remain in the membrane without removal.

Figure 10:
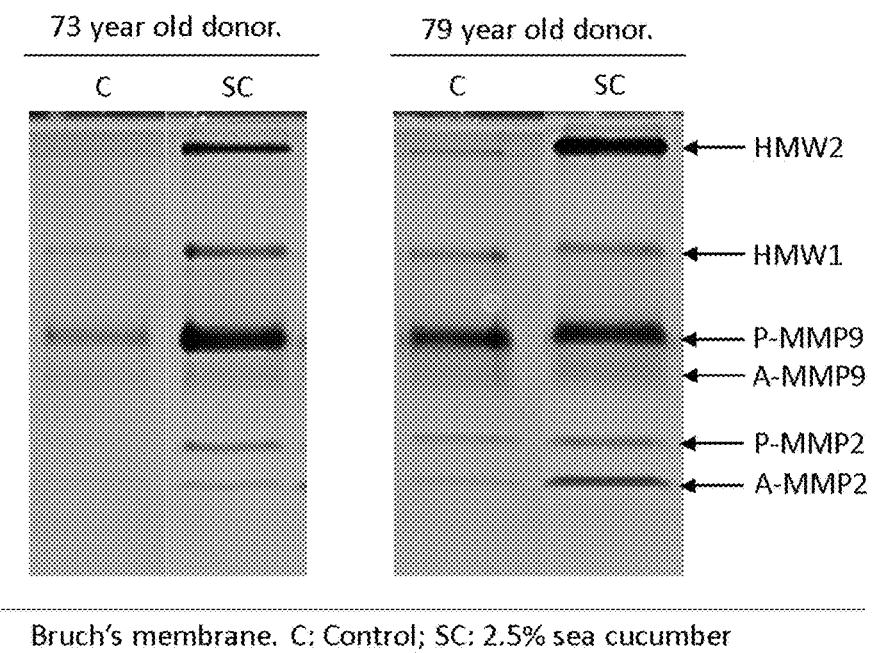
FIG. 10 shows the effect of a sea cucumber extract of the present invention on the removal of an MMP enzyme bound to a human Bruch's membrane.

To show if MMPs, which were bound to or trapped in the membrane, can be removed by a sea cucumber extract, Bruch's membranes isolated from the eyes of 73 and 79 year old donors were perfused with Tris-HCl for 12 hours to secrete and thereby remove the free MMP enzyme. Afterward, as a result of perfusion with a 2.5% sea cucumber extract, as shown in FIG. 10, it was confirmed that MMPs bound to the membrane are secreted.

Since HMW1 and HMW2 blocking the Bruch's membrane can be removed from the membrane, which can assist the transport ability of the Bruch's membrane, and the secretion of MMPs in an activated state has the effect of decomposing abnormal proteins, it is expected that this will give a positive influence on reversing the aging of the Bruch's membrane.

Example 5. Effect of Sea Cucumber Extract on Secretion of MMP Enzyme Present in Pellet of Bruch's Membrane of Human Eye To confirm the effect of sea cucumber extract on the secretion of the MMP enzyme from the Bruch's membrane, human Bruch's membranes isolated from both eyes of a 75-year-old donor were used. In a pellet of the Bruch's membrane used as a sample, the MMP enzymes were trapped in or bound to the membrane. As a control, a predetermined volume of a pellet was incubated with Tris-HCl buffer, and as an experimental group, a pellet was incubated with a 2.5% sea cucumber extract. After incubation at 37° C. for 24 hours, centrifugation was performed to measure an amount of MMPs secreted into a supernatant and MMPs present in a state of being bound to the pellet.

Figure 11:
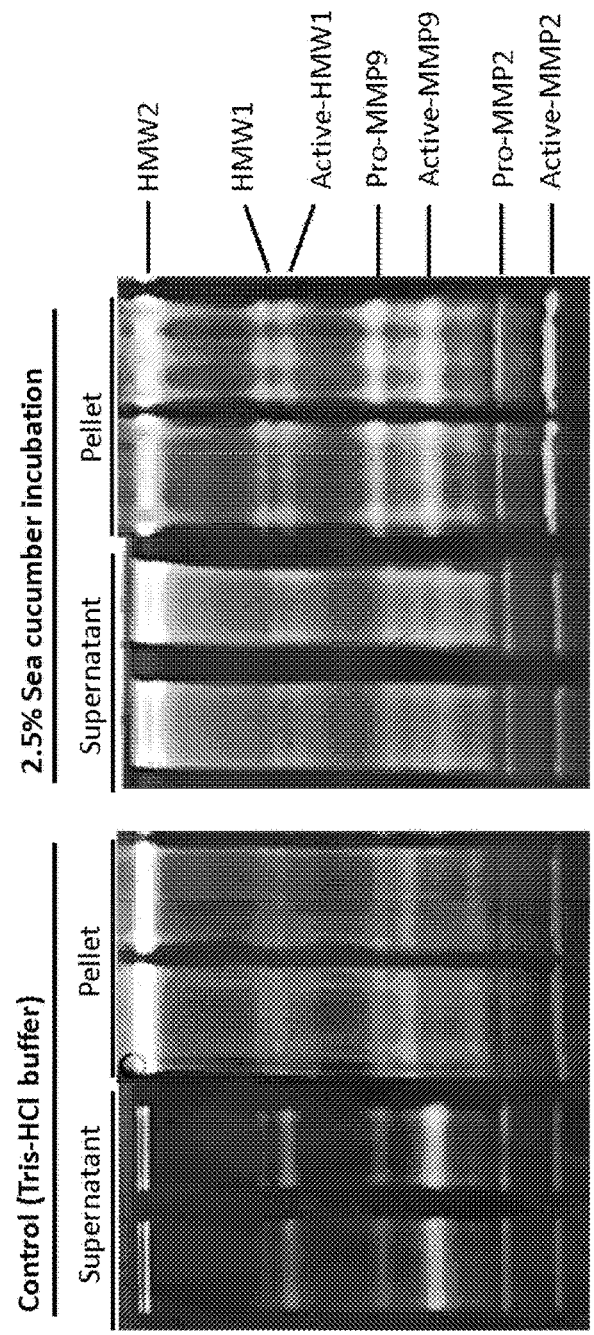
FIG. 11 shows the effect of a sea cucumber extract of the present invention on the removal of HMW2 bound to a human Bruch's membrane.

As a result, it can be confirmed that, while almost no HMW2 compound was secreted in the control, and most of the compound remained in the pellet, in the Bruch's membrane incubated with the sea cucumber extract, most of the HMW2 bound to the membrane was secreted into the supernatant (FIG. 11). This means that membrane flow was improved by removing the HMW2 blocking the membrane, resulting in improvement of the transport ability of the Bruch's membrane. In addition, it was confirmed that the incubation of the sea cucumber extract can give a positive influence on the improvement of a transport function by removing waste present in the Bruch's membrane by secreting activated HMW1, and pro-form-type pro-MMP2 and pro-MMP9 from the membrane.

Figure 12:
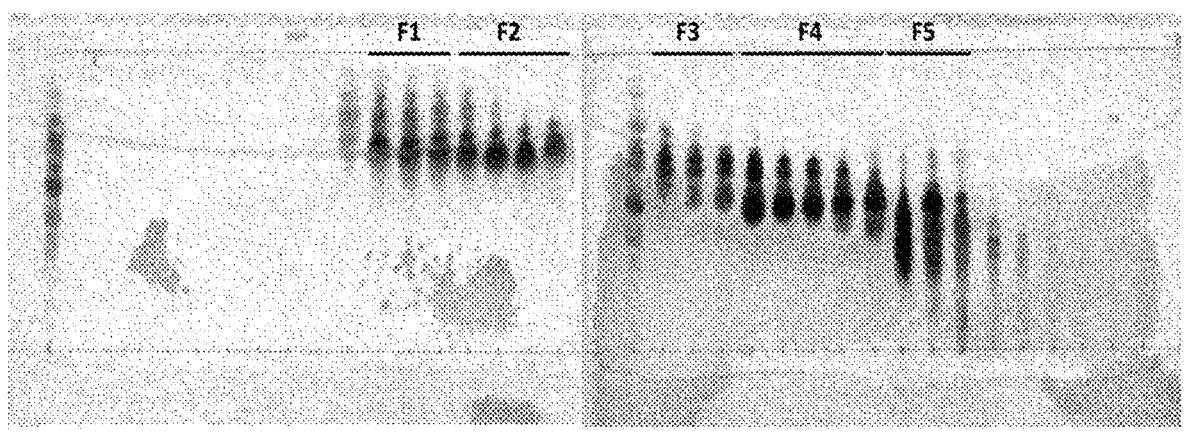
FIG. 12 shows a TLC result confirming a saponin of a fraction obtained by isolating a sea cucumber concentrate solution through a silica gel column.
Figure 13:
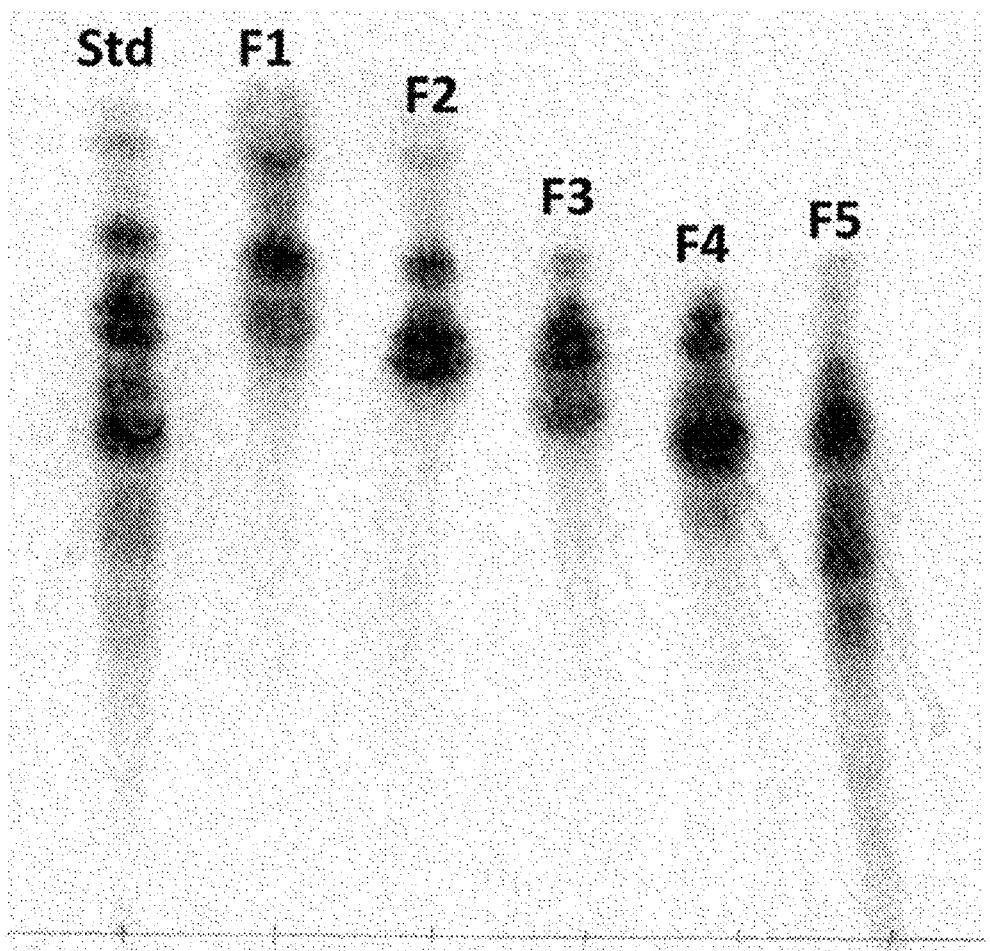
FIG. 13 shows a TLC result for the fractions of FIG. 12 after being divided into five groups of fractions consisting of similar components (Std, entire sea cucumber powder; F1~F5, fractions of sea cucumber powder).

Example 6. Effect of Fraction of Sea Cucumber Powder on Improvement in Hydraulic Conductivity of Human Bruch's Membrane Dried sea cucumber was grinded using a grinder, thereby preparing sea cucumber powder, 1.5 g of sea cucumber powder was dissolved in 15 mL of methanol, the solvent was evaporated, and 3 mL of a CMW (chloroform:methanol: H2O=50:30:6) solvent was added thereto to prepare a sea cucumber concentrate. 0.8 mL of the prepared sea cucumber concentrate was separated through a silica gel column. The column used the same CMW solvent as above and a total of 34 fractions were obtained once (about 2 mL) every 20 minutes. After the solvent was evaporated, each fraction was dissolved in 200 μL of methanol, and 5 μL each of the solution was obtained to quantify a saponin amount by TLC (FIG. 12). Consequently, as shown in FIG. 12 and Table 1, the fractions consisting of similar components were divided into 5 groups (F1~F5), each fraction group was subjected to TLC (FIG. 13). To equalize the amount of saponins present in five fractions, each group was diluted with a CMW solvent to normalize the saponin per fraction to a concentration of 250 μg/mL.

TABLE 1

| Type of fraction | Fraction No. | Amount of saponin (mg) |
| --- | --- | --- |
| F1 | 11, 12, 13 | 6.1 |
| F2 | 14, 15, 16, 17 | 11.4 |
| F3 | 18, 19, 20 | 7.7 |
| F4 | 21, 22, 23, 24, 25 | 19.7 |
| F5 | 26, 27, 28 | 17.5 |
| Total amount of saponin | | 62.4 |

To confirm the effect of sea cucumber powder on the improvement of fraction-specific hydraulic conductivity of the Bruch's membrane, the Bruch's membrane separated from the eye of a donor (78 or 82 years old) was subjected to measurement in the same manner as described in the hydraulic conductivity experimental method described in Example 2.

Figure 14:
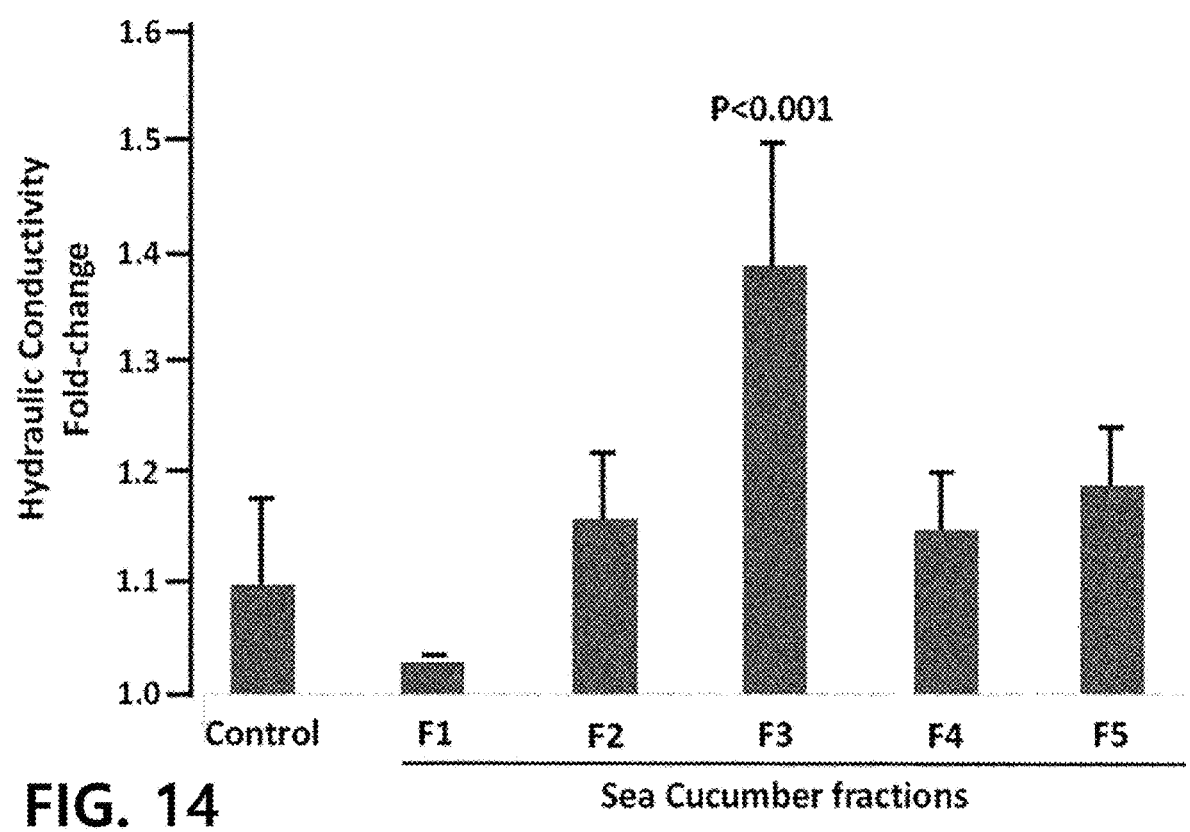
FIG. 14 shows the hydraulic conductivity-improving effect of the five fractions of FIG. 13.

Consequently, as shown in Table 2 and FIG. 14, the F3 fraction exhibited statistically significant improvement ($p<0.001$), F2, F4, and F5 also showed an increase in hydraulic conductivity, compared with the control.

TABLE 2

| Fraction | Degree of improvement of hydraulic conductivity (fold change, Comparison between before and after fraction incubation) Mean ± SD | Significance |
| --- | --- | --- |
| Control (Tris buffer) | 1.1 ± 0.08 (5) | |
| F1 | 1.03 ± 0.01 (3) | NS |
| F2 | 1.16 ± 0.06 (3) | NS |
| F3 | 1.39 ± 0.11 (3) | P < 0.001 |
| F4 | 1.15 ± 0.05 (3) | NS |
| F5 | 1.19 ± 0.05 (3) | NS |

Example 7. Identification of Active Ingredient Present in Sea Cucumber Powder

To identify a material specific to the F3 fraction exhibiting the greatest effect on the improvement of hydraulic conductivity of the Bruch's membrane in Example 6, types of saponins present in respective fractions were compared and analyzed.

Figure 15:
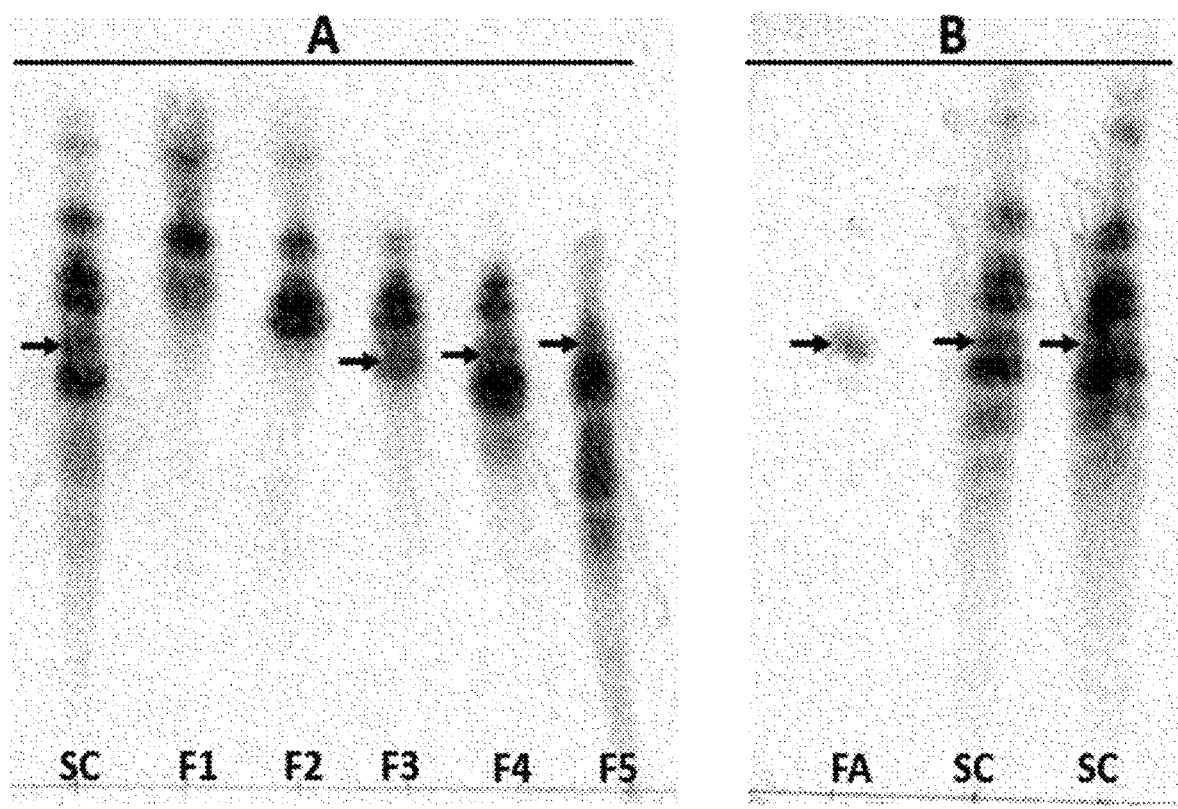
FIG. 15 shows the result of comparing saponin types included in respective fractions. (A) is the result of identifying a saponin type present in each sea cucumber fraction, and (B) is the result of comparing Frondoside A and saponins present in the entire sea cucumber extract (SC, entire sea cucumber; FA, Frondoside A; F1~F5, sea cucumber fractions).

In FIG. 15, a saponin present in F3 but not present in F1 and F2 was represented by an arrow (→), and it was shown to be present in a very small amount even in F4 and F5. This material was also found at the same position as the separation result of the whole sea cucumber sample (SC), and was identified to be Frondoside A (FA), which is conventionally known as a saponin.

Example 8. Effect of Sea Cucumber Fraction on MMP Secretion

To confirm the effect of the sea cucumber fraction on the secretion of MMPs from the Bruch's membrane, Bruch's membranes were isolated from eyes donated from patients ranging from 65 to 76 years of age. Specifically, 36 round samples of the Bruch's membrane, each having a diameter of 8 mm, were prepared, two circular pieces of the tissue (trephine) were added to each of the total of 18 test tubes, and then divided into a total of 6 groups (control, F1, F2, F3, F4, F5) each including three test tubes for the experiment. In the sea cucumber fraction, an amount of a saponin was adjusted equally at 250 µg/mL as described above, and after incubation for 24 hours, 50 µL of a culture solution was subjected to zymography to confirm MMP secretion. As a control, instead of a sea cucumber fraction, Tris buffer was added for incubation. The remaining culture solution was mixed with a CM solution (chloroform:methanol=2:1, v/v) to be used to analyze an amount of the lipid secreted in Example 9 below.

Figure 16:
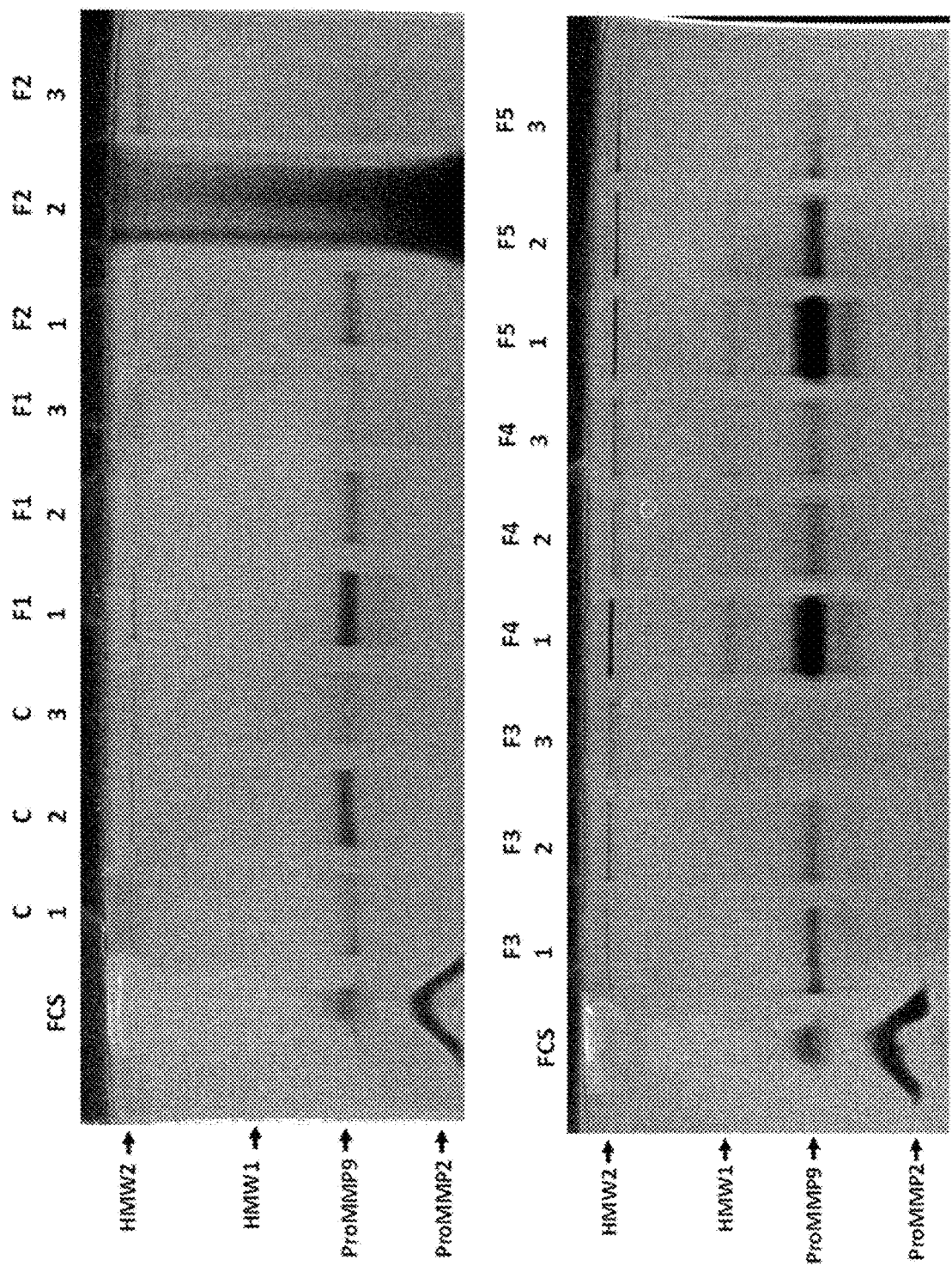
FIG. 16 is the result of confirming the secretion of an MMP enzyme from the Bruch's membrane after culturing a human Bruch's membrane with a sea cucumber fraction (F1~F5) (FCS, fetal calf serum; C, control; F1~F5, Bruch's membrane incubated with each fraction; each n=3)

Consequently, as shown in FIG. 16, in the control incubated with Tris buffer and the fraction F1, HMW2, Pro-MMP9, and a trace of HMW1 were secreted, but no pro-MMP2 was observed. It was confirmed that, in the fraction F3, compared with the control, Pro-MMP2 was additionally secreted, and in the fractions F4 and F5, HMW2, HMW1 and Pro-MMP2 were not only secreted from the membrane, but the secretion amount of Pro-MMP9 was also considerably increased. As a result, it can be seen that, in the fraction F3, the secretion amount of Pro-MMP2 was increased, and in the fractions F4 and F5, most types of the MMP enzymes bound to the Bruch's membrane were secreted.

Example 9. Effect of Lipid Change of Sea Cucumber Fraction

As shown in Example 8, after a Bruch's membrane was incubated with each sea cucumber fraction for 24 hours, a lipid component was extracted from 0.95 mL of the culture solution using a CM solution (chloroform:methanol=2:1, v/v). After the solvent was evaporated, 50 µL of the CM solution was added, and 30 µL of each sample was dropped onto a TLC plate to analyze the type of a lipid present in the plate.

Figure 17:
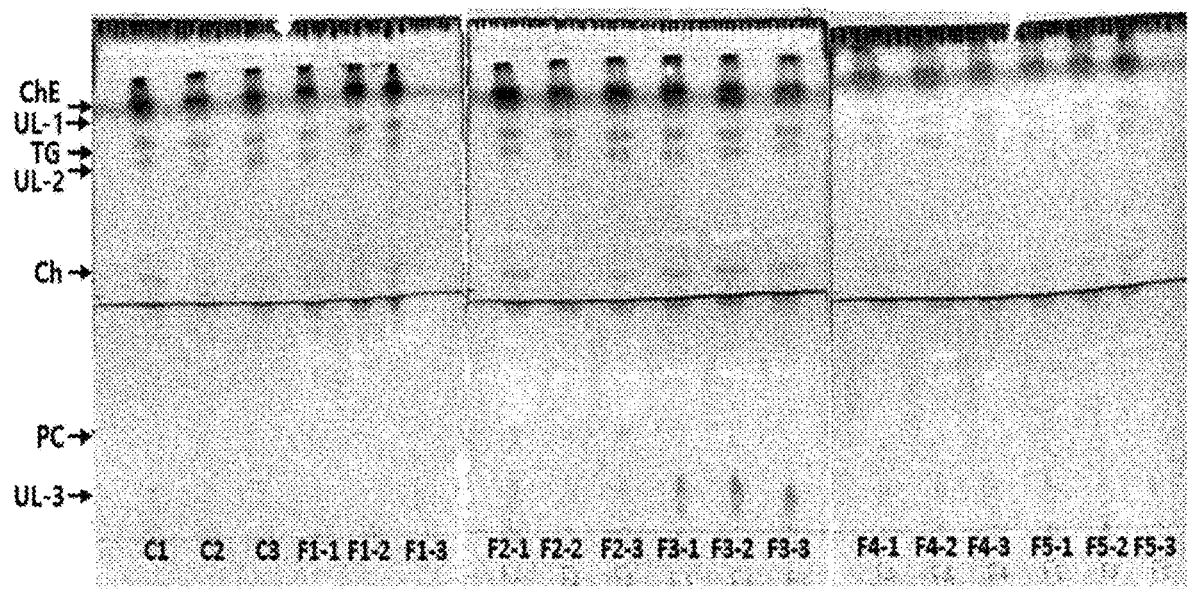
FIG. 17 is the result of analyzing a change of a lipid secreted after culturing with a sea cucumber fraction (ChE, cholesterol ester; TG, triglyceride; Ch, cholesterol; PC, phosphatidylcholine).

Consequently, as shown in FIG. 17, in the control and the fraction F 1, phosphatidylcholine (PC) was not secreted, but cholesterol esters (ChE) and triglycerides (TG) were secreted, and a trace amount of cholesterol (Ch) was secreted. Meanwhile, the fraction F3 was effective in secreting ChE, TG and Ch, and the removal of different lipid types UL-1 and UL-3. The fractions F4 and F5 had a slight effect on lipid removal, compared with the control.

Figure 18:
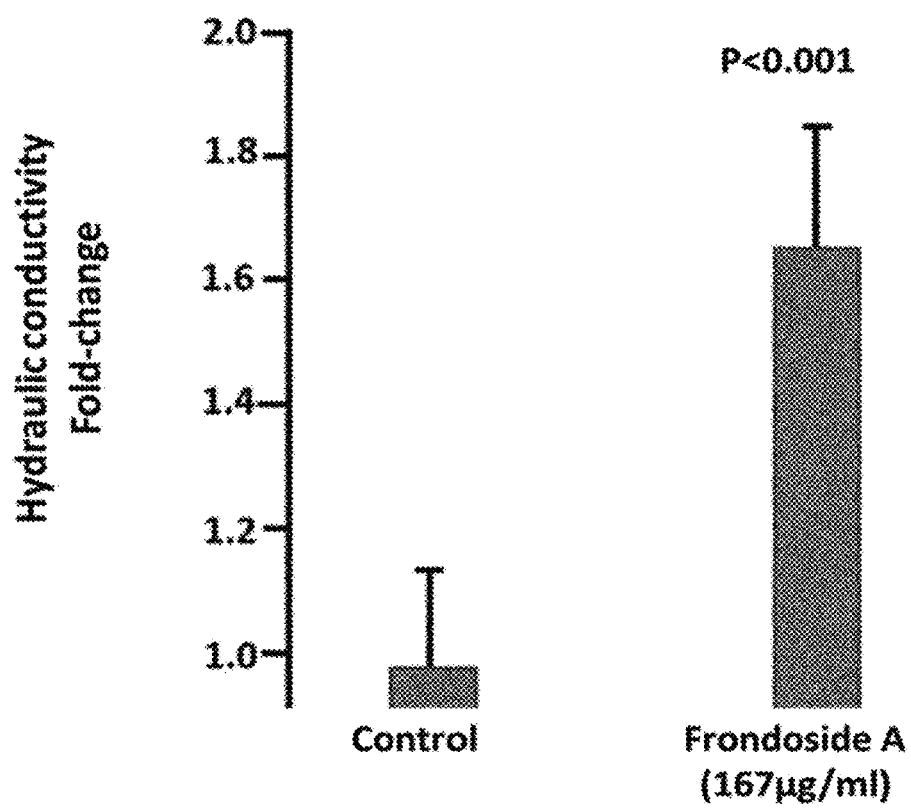
FIG. 18 is the result of confirming the effect of Frondoside A on the improvement of hydraulic conductivity.

Example 10. Effect of Frondoside a on Improvement of Hydraulic Conductivity in Human Bruch's Membrane The single saponin Frondoside A identified in Example 7 was used to confirm whether or not there is an effect of improving material transport ability in the human Bruch's membrane. Specifically, the change in hydraulic conductivity of 167 µg/mL of a Frondoside A solution was measured by the same method as described in the Examples using the Bruch's membrane of a donor patient (68 or 79 years old). As a control, Tris buffer was used. Consequently, as shown in Table 3 below and FIG. 18, it can be seen that the effect of Frondoside A on the improvement of hydraulic conductivity was 1.6-fold or higher than that of the control.

TABLE 3

| | Fold-change Mean ± SD (n) |
| --- | --- |
| Control (Tris buffer only) | 0.97 ± 0.16 (4) |
| Frondoside A (167 µg/ml) | 1.65 ± 0.2 (3)*** |

Example 11. Effect of Frondoside A on MMP Secretion

Zymography was performed using the solution incubated for 30 hours in the measurement of hydraulic conductivity in Example 10. Specifically, a Bruch's membrane was incubated with a Tris buffer solution as a control or a Frondoside A solution (167 µg/mL) for 30 hours, 50 µL of the resulting solution was mixed with 50 µL of the SDS sample buffer, and then 30 µL of the resulting mixture was loaded on a gel to measure an MMP enzyme secreted from a human Bruch's membrane.

Figure 19:
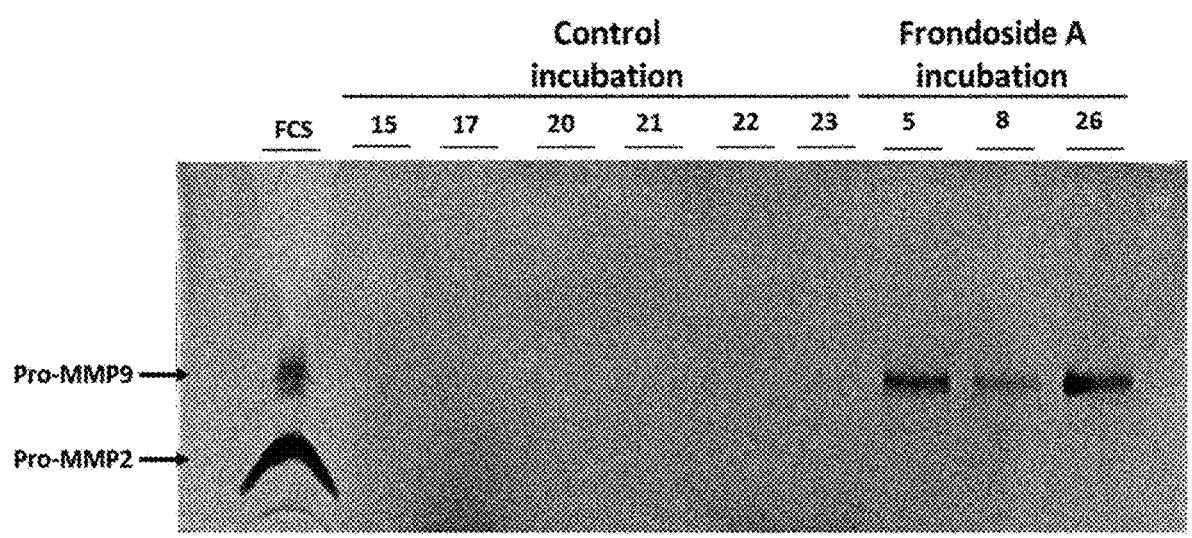
FIG. 19 is the result of confirming the effect of Frondoside A on the removal of MMPs from the Bruch's membrane.

Consequently, as shown in FIG. 19, it was confirmed that, when the Bruch's membrane was incubated with Tris buffer as a control, MMPs were rarely secreted, and when the Bruch's membrane was incubated with Frondoside A, an enormous amount of Pro-MMP9 bound to the membrane was secreted. From this, it can be seen that Frondoside A selectively binds with Pro-MMP9 among various types of MMPs, thereby removing the Pro-MMP9 from the Bruch's membrane.

Example 12. Lipid Removal Effect of Frondoside A

To confirm the lipid removal effect of Frondoside A, after the measurement of hydraulic conductivity in Example 10, the Bruch's membrane was cut into a piece having a diameter of 6 mm, and then a lipid was extracted using a CM solution (chloroform:methanol=2:1), followed by evaporating the solvent. After 50 µL of a CM solution was added thereto again, 40 µL of the resulting solution was dropped on a silica gel TLC plate, and the type and amount of the lipid were analyzed.

Figure 20:
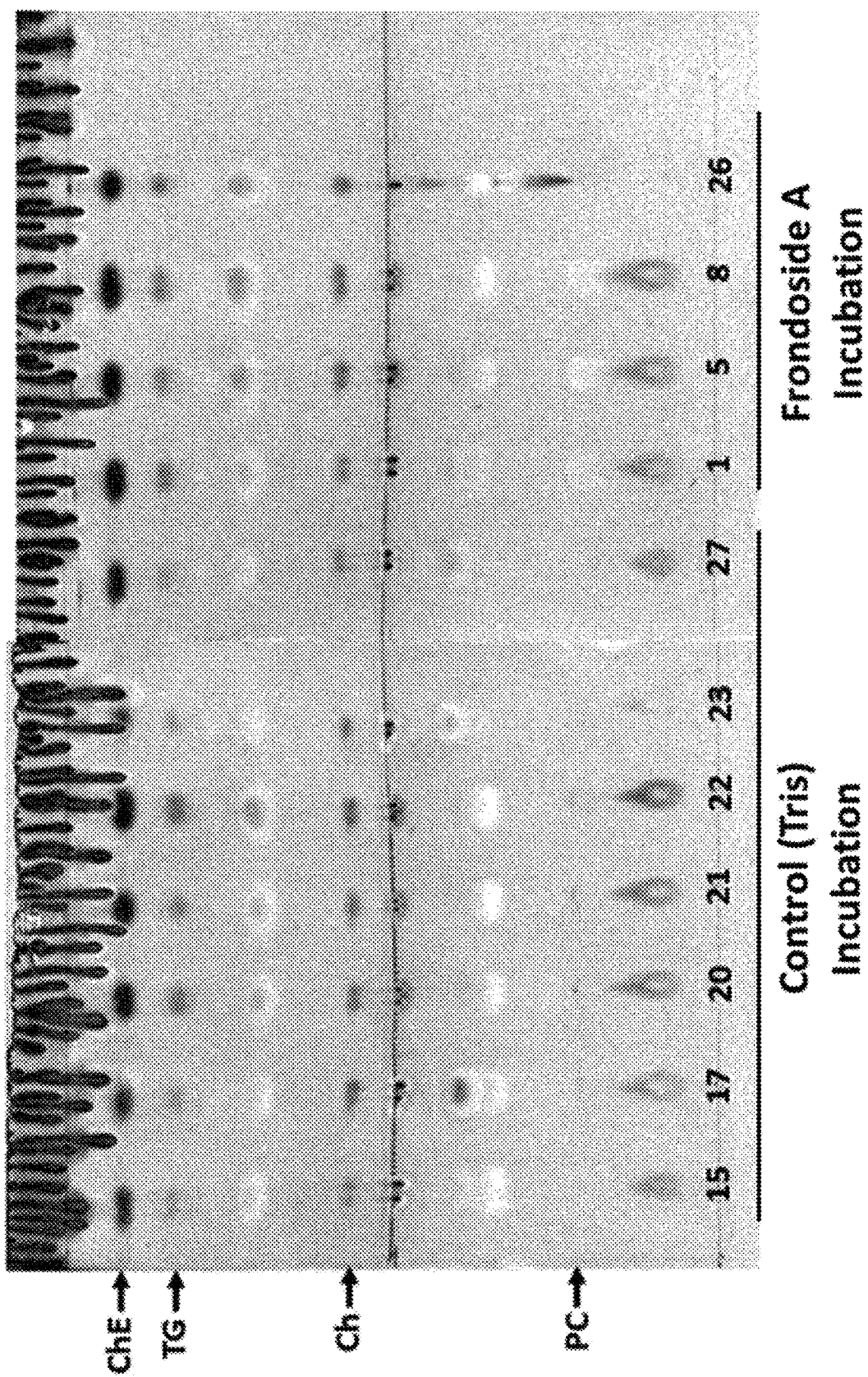
FIG. 20 is the result of confirming the effect of Frondoside A on the removal of a lipid from the Bruch's membrane.

Consequently, as shown in FIG. 20, it was confirmed that, when the Bruch's membrane was incubated with Frondoside A, it did not have an effect of removing ChE, TG and Ch, but had an effect of removing phosphatidylcholine from the Bruch's membrane.

The invention claimed is:

1. A method for preventing, delaying and treating a Bruch's membrane dysfunction-associated disease, the method comprising:
    administering to a subject in need thereof, an extract or fraction of sea cucumber as an active ingredient, wherein the Bruch's membrane dysfunction-associated disease is selected from the group consisting of age-related macular degeneration (AMD), Sorsby's fundus dystrophy, Malattia Levintanese (ML), Stargardt disease, Best's vitelliform retinal dystrophy and Doyne's honeycomb retinal dystrophy (DHRD), which are due to a dysfunction of the Bruch's membrane.

2. The method according to claim 1, wherein the active ingredient improves the transport function of the Bruch's membrane.

3. The method according to claim 2, wherein the transport function is improved by improving the hydraulic conductivity of the Bruch's membrane.

4. The method according to claim 2, wherein the transport function is improved by improving the material diffusion function of the Bruch's membrane.

5. The method according to claim 2, wherein the transport function is improved by removing a protein or lipid bound to or trapped in the Bruch's membrane.

6. The method according to claim 1, wherein the active ingredient regenerates the Bruch's membrane and improves the functions of the Bruch's membrane.

7. The method according to claim 6, wherein the active ingredient regenerates the Bruch's membrane and improves the functions of the Bruch's membrane by removing high molecular weight complex 1 (HMW1) and high molecular weight complex 2 (HMW2) or a lipid component bound to or deposited on the Bruch's membrane.

8. The method according to claim 6, wherein the active ingredient regenerates Bruch's membrane and improves the functions of the Bruch's membrane by secreting pro-matrix metalloproteinase 2 (pro-MMP2), pro-matrix metalloproteinase 9 (pro-MMP9), active matrix metalloproteinase 2 (active-MMP2) and active matrix metalloproteinase 9 (active-MMP9) from the matrix of the Bruch's membrane.

9. The method according to claim 6, wherein the active ingredient regenerates the Bruch's membrane and improves the functions of the Bruch's membrane by activating the secretion of active MMPs from the retinal pigment epithelium (RPE).

10. The method according to claim 1, wherein the active ingredient includes Frondoside A.

11. The method according to claim 1, wherein the method further comprises administering Frondoside A.

12. The method according to claim 1, wherein the method further includes administering one or more selected from the group consisting of an amino acid, an antioxidant material, a mineral, a metallic material, lutein, astaxanthin and zeaxanthin.

13. A method for preventing, delaying and treating a Bruch's membrane dysfunction-associated disease, the method comprising:
    administering to a subject in need thereof, Frondoside A, an isomer thereof, a hydrate thereof or a salt thereof as an active ingredient, wherein the Bruch's membrane dysfunction-associated disease is selected from the group consisting of age-related macular degeneration (AMD), Sorsby's fundus dystrophy, Malattia Levintanese (ML), Stargardt disease, Best's vitelliform retinal dystrophy and Doyne's honeycomb retinal dystrophy (DHRD), which are due to a dysfunction of the Bruch's membrane.

14. The method according to claim 13, wherein the active ingredient is derived from sea cucumber.

15. The method according to claim 13, wherein the active ingredient improves the transport function of the Bruch's membrane by removing Pro-MMP9 or phosphatidylcholine bound to or trapped in the Bruch's membrane.

* * * * *